(12) United States Patent
Kostic et al.

(10) Patent No.: US 11,638,550 B2
(45) Date of Patent: May 2, 2023

(54) SYSTEMS AND METHODS FOR STROKE DETECTION

(71) Applicant: Stryker Corporation, Kalamazoo, MI (US)

(72) Inventors: Marko N. Kostic, Portage, MI (US); Sean Hadley, Christchurch (NZ); Richard L. Friedland, Sarasota, FL (US)

(73) Assignee: Stryker Corporation, Kalamazoo, MI (US)

( * ) Notice: Subject to any disclaimer, the term of this patent is extended or adjusted under 35 U.S.C. 154(b) by 719 days.

(21) Appl. No.: 15/200,818

(22) Filed: Jul. 1, 2016

(65) Prior Publication Data

US 2017/0007167 A1 Jan. 12, 2017

Related U.S. Application Data

(60) Provisional application No. 62/189,258, filed on Jul. 7, 2015.

(51) Int. Cl.
*A61B 5/00* (2006.01)
*A61B 5/0205* (2006.01)
(Continued)

(52) U.S. Cl.
CPC .......... *A61B 5/4064* (2013.01); *A61B 5/0077* (2013.01); *A61B 5/112* (2013.01);
(Continued)

(58) Field of Classification Search
CPC combination set(s) only.
See application file for complete search history.

(56) References Cited

U.S. PATENT DOCUMENTS 6,280,390 B1   8/2001   Akselrod et al.
6,331,162 B1   12/2001  Mitchell
(Continued)

FOREIGN PATENT DOCUMENTS

EP    0443267 A1   8/1991
WO    9220273      11/1992
(Continued)

OTHER PUBLICATIONS

A. Mohd Nor et. al. ("Agreement Between Ambulance Paramedic- and Physician-Recorded Neurological Signs With Face Arm Speech Test (FAST) in Acute Stroke Patients," Mar. 9, 2004).*
(Continued)

*Primary Examiner* — Scott Luan
(74) *Attorney, Agent, or Firm* — Warner Norcross + Judd LLP

(57) ABSTRACT

A stroke detection device includes a cell phone having a sensor adapted to sense a characteristic of the user of the cell phone. An app executed by the cell phone passively monitors the characteristic to determine if the user has experienced a stroke. The app requests that the user take one or more tests using the cell phone if the presence of a stroke is possible. The tests include the user speaking a specific phrase into the cell phone that is compared to a previously recorded sound sample of the user; the user taking a picture of himself or herself with the cell phone that the app compares to a previous picture of the user; and the user attempting to hold his or her arm out straight while holding the cell phone wherein accelerometers in the phone measure the steadiness of his or her arm.

11 Claims, 16 Drawing Sheets

(51) Int. Cl.
*A61B 5/01* (2006.01)
*H04M 1/02* (2006.01)
*A61B 5/11* (2006.01)
*A61B 5/021* (2006.01)
*A61B 5/024* (2006.01)

(52) U.S. Cl.
CPC .......... *A61B 5/6803* (2013.01); *A61B 5/6898* (2013.01); *A61B 5/7282* (2013.01); *A61B 5/742* (2013.01); *H04M 1/0202* (2013.01); *A61B 5/0022* (2013.01); *A61B 5/01* (2013.01); *A61B 5/021* (2013.01); *A61B 5/02055* (2013.01); *A61B 5/02438* (2013.01); *A61B 5/681* (2013.01)

(56) References Cited

U.S. PATENT DOCUMENTS

| | | | |
|---|---|---|---|
| 6,577,884 B1 | 6/2003 | Boas | |
| 7,674,231 B2 | 3/2010 | McCombie et al. | |
| 7,803,120 B2 | 9/2010 | Banet et al. | |
| 8,060,189 B2 | 11/2011 | Ben Dor et al. | |
| 8,180,437 B2 | 5/2012 | Ohki et al. | |
| 8,655,004 B2 | 2/2014 | Prest et al. | |
| 8,788,005 B1 | 7/2014 | Cheng | |
| 9,782,122 B1* | 10/2017 | Pulliam | A61B 5/4824 |
| 9,962,104 B2 | 5/2018 | De Vries et al. | |
| 2005/0027173 A1* | 2/2005 | Briscoe | G06F 19/325 |
| | | | 600/300 |
| 2007/0112277 A1 | 5/2007 | Fischer et al. | |
| 2009/0005654 A1* | 1/2009 | Jung | A61B 5/1101 |
| | | | 600/300 |
| 2009/0227890 A1* | 9/2009 | Lanfermann | A61B 5/4824 |
| | | | 600/555 |
| 2011/0118564 A1 | 5/2011 | Sankai | |
| 2013/0182144 A1* | 7/2013 | Klinghult | H04N 5/23229 |
| | | | 348/231.2 |
| 2013/0245389 A1* | 9/2013 | Schultz | A61B 5/0002 |
| | | | 600/301 |
| 2014/0188516 A1* | 7/2014 | Kamen | G06F 19/3406 |
| | | | 705/3 |
| 2014/0316229 A1 | 10/2014 | Tognetti et al. | |
| 2015/0018660 A1* | 1/2015 | Thomson | A61B 5/0404 |
| | | | 600/393 |
| 2015/0087952 A1* | 3/2015 | Albert | A61B 5/04085 |
| | | | 600/384 |
| 2015/0209207 A1* | 7/2015 | Cooper | A61G 5/1056 |
| | | | 701/49 |
| 2016/0015324 A1* | 1/2016 | Du Bois | A61B 5/6898 |
| | | | 600/538 |
| 2016/0088136 A1* | 3/2016 | Di Donato | H04M 1/21 |
| | | | 600/365 |
| 2016/0331255 A1* | 11/2016 | Cheatham, III | A61B 5/046 |
| 2017/0195637 A1 | 6/2017 | Kusens et al. | |
| 2018/0189946 A1 | 7/2018 | Kusens et al. | |

FOREIGN PATENT DOCUMENTS

| | | |
|---|---|---|
| WO | 2007047667 A2 | 4/2007 |
| WO | 2013001265 A2 | 1/2013 |
| WO | 2014096920 A1 | 6/2014 |
| WO | 2014165049 A1 | 10/2014 |
| WO | 2016074648 A1 | 5/2016 |

OTHER PUBLICATIONS

How Medical Equipment Works Explained Simply downloaded from www.howequipmentworks.com, available at least as of Aug. 20, 2014.

Gallagher, Shaun, "Smartphone Sensor Data Mining for Gait Abnormality Detection", Master's thesis submitted in partial fulfillment of the requirements for the degree of Master of Sciences in the department of computer science at Fordham University, dated Feb. 2014, pp. 1-67.

* cited by examiner

SYSTEMS AND METHODS FOR STROKE DETECTION

CROSS-REFERENCE TO RELATED APPLICATIONS

This application claims priority to U.S. provisional patent application Ser. No. 62/189,258 filed Jul. 7, 2015, by inventors Sean Hadley et al. and entitled SYSTEMS AND METHODS FOR STROKE DETECTION, the complete disclosure of which is incorporated herein by reference.

BACKGROUND

The present disclosure relates to systems and methods for detecting medical strokes in individuals.

Strokes are cerebrovascular events that cause temporary or permanent loss of brain functions. It is estimated that there are approximately 800,000 cases of symptomatic strokes per year in the United States alone, and ten or more million asymptomatic, or silent, strokes per year. When a stroke occurs, it is critical that prompt medical attention is received in order to potentially reduce the severity of the stroke and/or to prevent permanent tissue loss. Patients who experience a stroke, however, often do not seek prompt medical attention due to a variety of factors, including not recognizing that a stroke has occurred, not realizing the importance of prompt treatment, misperceiving the symptoms of stroke as temporary or due to other causes, or for still other reasons.

SUMMARY

Some of the embodiments of the present disclosure address the past difficulties with stroke sufferers not timely seeking medical assistance when their bodies show signs of a potential stroke. That is, the present disclosure describes a stroke detection device that is adapted to encourage users to seek prompt medical assistance when they experience one or more symptoms that are suggestive of a stroke. In some embodiments, the stroke detection device passively monitors one or more characteristics of the user and provides notification to the user of a potential stroke when the passive monitoring detects an event suggestive of a stroke. Prior to seeking medical assistance, the stroke detection device may issue instructions for the user to take one or more tests using the stroke detection device to better assess whether the user has experienced a stroke or not. If the tests are suggestive of a stroke, the user is instructed to seek prompt medical assistance. In some embodiments, the device automatically contacts a monitoring center and/or medical facility.

According to one embodiment, a stroke detection device is provided that includes a cell phone and a cell phone app. The cell phone includes a controller, a memory, and a sensor. The sensor is adapted to sense a characteristic of a user of the cell phone. The app is stored in the memory and is adapted to be executed by the controller. When executed, the app causes the controller to passively monitor the characteristic to determine if the user may have experienced a stroke.

In some embodiments, the app is further configured to notify the user if the characteristic indicates that the user may have experienced a stroke. The app may also request the user to take a plurality of tests using the stroke detection device. The tests include any one or more of the following:
(a) the user speaking a specific phrase into a microphone of the cell phone wherein the controller compares a current sound sample generated from the user speaking the specific phrase into the microphone to a past sound sample of the user speaking the specific phrase;
(b) the user making a requested facial expression while a current image of the user is captured by an image sensor of the cell phone, wherein the controller compares the current image of the user to a past image of the user; and
(c) the user attempting to hold his or her arm out straight while holding the cell phone and the controller monitors outputs from an accelerometer within the cell phone while the user attempts to hold his or her arm out straight.

In some embodiments, the sensor of the stroke detection device is an accelerometer and the characteristic monitored by the sensor is a gait of the cell phone user. The accelerometer may also or alternatively be used to monitor a steadiness of the users hand while using the cell phone.

In some embodiments, the sensor is a microphone and the monitored characteristic is a speech quality of the user.

An auxiliary device is included, in some embodiments, that communicates with the cell phone. The auxiliary device is adapted to forward data to the app and the app is configured to use the data when determining if the user may have experienced a stroke. In some embodiments, the auxiliary device is a cell phone case that includes a plurality of auxiliary sensors that generate the data. The auxiliary sensors include temperature sensors adapted to sense a temperature of the user when the user contacts the auxiliary sensors. The app may be configured to determine which of the auxiliary sensors is in contact with the users right hand and which of the auxiliary sensors is in contact with the users left hand. In doing so, the app may utilize information from an accelerometer inside the cell phone to determine which of the auxiliary sensors is in contact with the users right hand and which of the auxiliary sensors is in contact with the users left hand.

The cell phone case may also, or alternatively, include a plurality of ECG electrodes coupled to the cell phone case and adapted to send the data to the controller. The ECG electrodes are used to determine if the user is experiencing atrial fibrillation.

The plurality of auxiliary sensors communicates with the controller via a cable plugged into a microphone jack of the cell phone, or a cable plugged into the Universal Serial Bus (USB) of the cell phone, in some embodiments.

Alternatively, the auxiliary device is a bracelet having a heart rate sensor coupled thereto and a wireless transceiver. The heart rate sensor generates the data and the wireless transceiver communicates the data to the cell phone. The bracelet may include a blood pressure sensor enabling the wireless transceiver to communicate blood pressure information to the cell phone.

In yet another alternative, the auxiliary device is a user-wearable device that includes a pulse wave velocity sensor and a wireless transceiver. The pulse wave velocity sensor generates the data and the wireless transceiver communicates the data to the cell phone. The auxiliary device may also include a controller adapted to utilize the pulse wave velocity readings from the pulse wave velocity sensor to determine a blood pressure of the user. The wireless transceiver communicates the determined blood pressure to the cell phone.

In some embodiments, the auxiliary device is a pair of eyeglasses having a first temperature sensor and a second temperature sensor. The first temperature sensor is coupled to the eyeglasses at a first position that measures the users temperature on a first side of the user's head, and the second temperature sensor is coupled to the eyeglasses at a second position that measures the users temperature on a second side of the user's head. The eyeglasses include a wireless transceiver adapted to transmit temperature data to the app. The temperature data includes information regarding a difference between the user's temperature on the first side of the users head and the users temperature on the second side of the users head.

The auxiliary device may also be a mattress having a plurality of sensors adapted to detect movement of the user while the user sleeps on the mattress. As yet another alternative, the auxiliary device may be a person support apparatus (e.g. bed, stretcher, recliner, chair, cot, etc.) having a plurality of sensors adapted to detect movement of the user while the user is supported on the person support apparatus. When implemented as a person support device, the plurality of sensors include a plurality of load cells, in at least one embodiment, that are adapted to sense a weight of the user while the user is supported on the person support apparatus.

In still other embodiments, the auxiliary device is a steering wheel of an automobile having a plurality of temperature sensors coupled thereto.

According to another embodiment, a stroke detection device is provided that includes a temperature sensor adapted to take temperature readings of a users temperature and a controller. The controller is in communication with the temperature sensor and is adapted to automatically distinguish between a temperature reading from the temperature sensor that is taken from a right side of the users body and a temperature reading from the temperature sensor that is taken from a left side of the user's body.

The controller is adapted to compare the temperature reading from the right side of the user's body to the temperature reading from the left side of the users body. The controller requests that the user take a test using the stroke detection device, in some embodiments, if the temperature reading from the right side of the users body differs from the temperature reading from the left side of the users body by more than a threshold.

The test may include the user speaking a phrase into a microphone coupled to the controller wherein the controller compares a current sound sample generated from the user speaking the phrase into the microphone to a past sound sample of the user speaking the phrase. The controller detects if the user omits a word, or a portion of a word, in the phrase in the current sound sample and/or the controller detects if the user slurs one or more words in the phrase.

The test may alternatively include the user making a requested facial expression while a current image of the user is captured by an image sensor. The controller compares the current image of the user to a past image of the user and detects if any facial droop is present in the current image of the user. The controller may instruct the user to smile before the current image is taken and then compare the captured image of the smiling user to an image previously captured while the user was smiling.

As yet another alternative, the test may include the user attempting to hold each arm out straight while the user holds the stroke detection device in his or her hand. The stroke detection includes an accelerometer in communication with the controller that detects movement while the user attempts to hold each arm out straight.

In some embodiments, the stroke detection device includes a cellular telephone network transceiver within the housing. The cellular telephone network transceiver is in communication with the controller whereby the controller is able to convey audio signals from a microphone of the stroke detection device to a cellular telephone network.

According to another embodiment, a stroke detection device is provided that includes a microphone, a memory, and a controller. The microphone converts first acoustic waves from a user's voice into first audio signals. The memory contains a file of a baseline characteristic of the users voice. The controller determines a current characteristic of the user's voice from the first audio signals, compares the current characteristic to the baseline characteristic, and issues a notification to the user if the comparison indicates that the user may have experienced a stroke.

The stroke detection device further includes a speaker adapted to convert second audio signals received from a remote recipient into second acoustic waves, in some embodiments. The controller transmits the first audio signals to the remote recipient.

In some embodiments, the stroke detection device includes a WiFi radio in communication with the controller whereby the controller conveys the first audio signals to a remote computer network using the WiFi radio. The baseline characteristic includes at least one of the following: speed, volume, pitch, emphasis, and pronunciation.

A display may also be included in the device that communicates with the controller. The controller issues the notification using the display. The instructions correspond to a test to be taken by the user using the stroke detection device. The controller evaluates results from the test after the user has taken the test, determines if the results indicate that the user may have experienced a stroke and, if so, issues second instructions on the display for taking a second test using the stroke detection device.

In some embodiments, the stroke detection device includes an auxiliary device, such as a watch, bracelet, patch, or pair of eyeglasses, that has a heart rate sensor coupled thereto and a wireless transceiver. The heart rate sensor generates data and the wireless transceiver communicates the data to the controller. The auxiliary device may also include a blood pressure sensor. When so included, the wireless transceiver communicates blood pressure information to the controller.

The auxiliary device is a user-wearable pulse wave velocity sensor, in some embodiments. The user-wearable pulse wave velocity sensor generates pulse wave velocity data that the wireless transceiver communicates to the controller. The pulse wave velocity sensor may include a controller that utilizes the pulse wave velocity readings to determine a blood pressure of the user. The wireless transceiver communicates the blood pressure to the controller.

In yet another embodiment, a stroke detection device is provided that includes a main device and an auxiliary device. The main device includes a main controller, a main memory, a main sensor, and a main display. The main controller executes a software application selected by a user of the main device that is stored in the main memory. The main sensor detects a first characteristic of the user. The auxiliary device is spaced from the main device and in communication with the main device. The auxiliary device includes an auxiliary sensor adapted to detect a second characteristic of the user. The auxiliary device transmits data regarding the second characteristic to the main device. The main device issues a notification on the main display if either of the first or second characteristics indicates that the user may have experienced a stroke.

In some embodiments, the main device is one of a tablet computer, a laptop computer, a desktop computer, and a cell phone.

The user-wearable device includes circuitry adapted to respond to a near field interrogation signal emitted from the main device with a message, in some embodiments. The message includes the data regarding the second characteristic.

The main device further includes a main keyboard in some embodiments. The main sensor includes a plurality of pressure sensors and the first characteristic is a force profile of the users use of the main keyboard. The main keyboard may be a virtual keyboard displayed on the main display or it may be a physical keyboard. The main keyboard also or alternatively includes a plurality of temperature sensors. When so included, the first characteristic is a temperature difference between the user's right and left hands as determined by the temperature sensors when the user is using the main keyboard.

According to another embodiment, a stroke detection device is provided that includes a first temperature sensor and a second temperature sensor, a memory, and a controller. The first and second temperature sensors detect a temperature of a user of the stroke detection device based upon contact with the users fingers. The memory contains a plurality of software applications. The controller executes at least one of the software applications selected by the user. Further, the controller determines a difference between a first temperature reading from the first temperature sensor and a second temperature reading from the second temperature sensor and issues a notification that the user may have experienced a stroke if the difference exceeds a threshold.

The stroke detection device is configured to automatically communicate with a remote recipient if the controller determines that the user has failed one of more tests. The automatic communication may include a voice message, a text message, and/or an email. The remote recipient is a monitoring center, in at least one embodiment, that has one or more computers in communication with a computer network of a hospital. The automatic communication includes transmitting a user code to the monitoring center that is used by the monitoring center to identify the user. The monitoring center forwards to the computer network of the hospital the identity of the user. The automatic communication with the remote recipient also includes transmitting a current location of the stroke detection device, in at least some embodiments. The current location of the stroke detection device is determined by the controller.

The first and second temperature sensors are housed inside of a cell phone case, in some embodiments. The first temperature sensor is positioned on a first side of the cell phone case and the second temperature sensor is positioned on a second side of the cell phone case.

In other embodiments, the first and second temperature sensors are housed inside of an automobile steering wheel. In still other embodiments, the first and second temperature sensors are housed inside of a case adapted to be coupled to a tablet computer.

According to yet another embodiment, a stroke detection device is provided that includes an image sensor, an accelerometer, a microphone, a memory, and a controller. The memory contains a plurality of software applications and the controller is adapted to execute the plurality of software applications. At least one of the software applications causes the controller, when executed, to perform at least one of a facial test, arm test, and speech test. In some embodiments, the software application performs at least one of the facial, arms, and speech tests in response to a triggering event detected by the software application. The triggering event includes a change in the user's gait as detected by the controller using outputs from the accelerometer. The triggering event also includes a change in a speech pattern of the user as detected by the controller using outputs from the microphone. The triggering event may also include a message received by the controller from an auxiliary device.

In yet another embodiment, a non-transitory, tangible, computer readable storage medium having instructions stored therein is provided. The instructions, when executed by a computer, cause the computer to perform at least two of the following functions: (a) compare a current sound sample generated from the user speaking a specific phrase into a microphone to a past sound sample of the user speaking the specific phrase; (b) compare a current image of the user to a past image of the user; and (c) monitor movement of the user's arms while the user attempts to hold his or her arms out straight.

Before the various embodiments disclosed herein are explained in detail, it is to be understood that the claims are not to be limited to the details of operation or to the details of construction and the arrangement of the components set forth in the following description or illustrated in the drawings. The embodiments described herein are capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the claims to any specific order or number of components. Nor should the use of enumeration be construed as excluding from the scope of the claims any additional steps or components that might be combined with or into the enumerated steps or components.

DETAILED DESCRIPTION OF THE EMBODIMENTS

Figure 1:
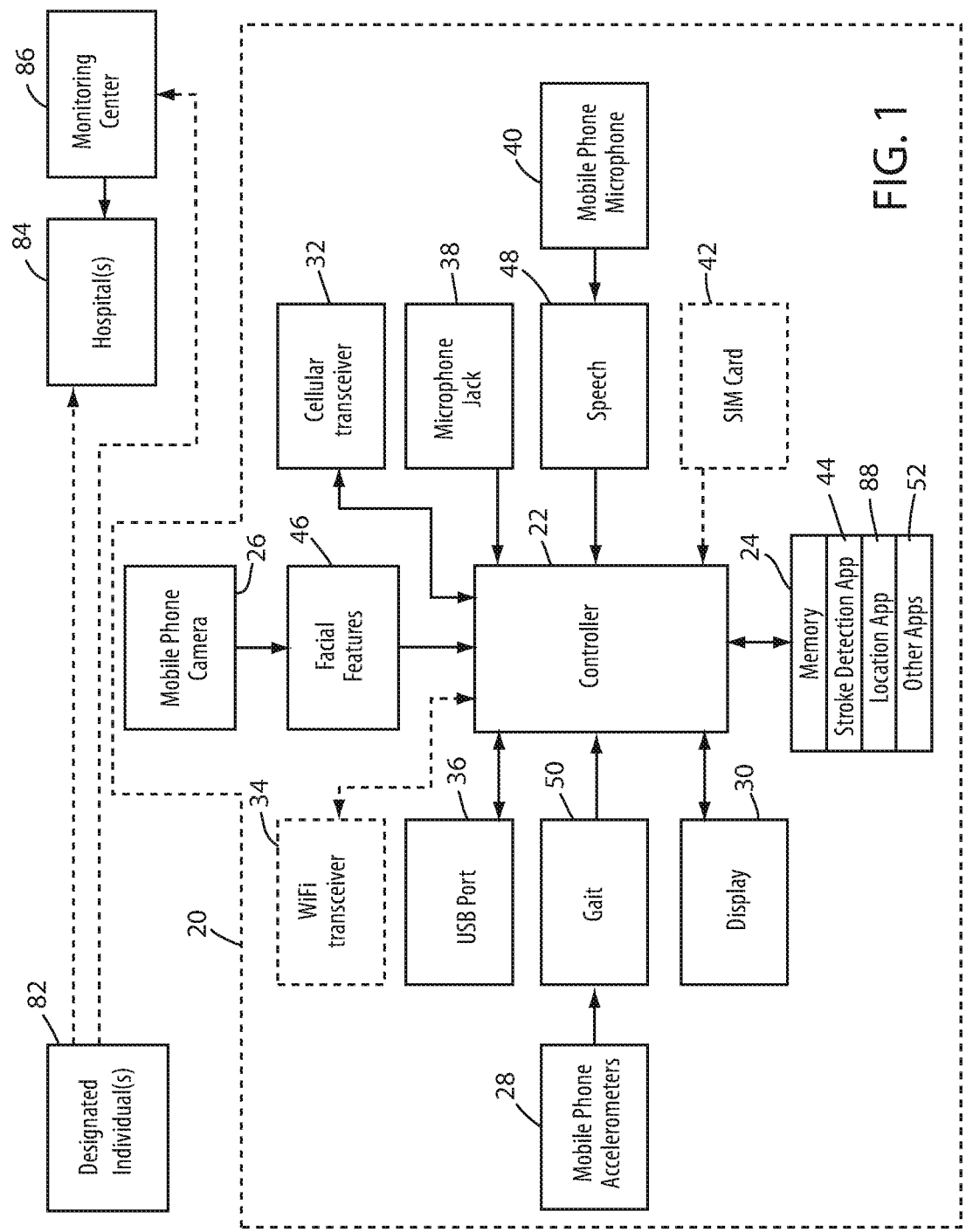
FIG. 1 is a block diagram of a first embodiment of a stroke detection device according to the present disclosure.

A stroke detection device 20 according to a first embodiment of the disclosure is shown in FIG. 1. Stroke detection device 20 of FIG. 1 is implemented as a cell phone in the embodiment shown in FIG. 1. As will be discussed in greater detail below, stroke detection device 20 can be implemented in other forms, including tablet computers, laptop computers, and/or desktop computers, and still other forms. Regardless of the specific physical form in which stroke detection device 20 is implemented, it is configured to assist a user in detecting when the user may have experienced a stroke, and to help ensure that the user seeks prompt medical assistance when appropriate. For purposes of the following description, the use of the term "stroke" will also include transient ischemic attacks, which are sometimes referred to as "mini-strokes."

In some embodiments, the stroke detection device 20 passively monitors one or more characteristics of the user while the user uses the stroke detection device in its normal and customary manner. For example, when stroke detection device 20 is implemented as a cell phone, the stroke detection device 20 passively monitors one or more user characteristics while the user makes and receives phone calls, while the user sends and receives electronic communications (texts, emails, Internet service messages,), visits websites on the Internet, and engages in other normal cell phone activity. If the stroke detection device 20 detects an abnormality in a user characteristic during this normal usage, the device 20 alerts the user and requests that the user take one or more additional tests using the device 20. The device analyzes the results of those tests and urges the user, in some embodiments, to seek medical assistance if the tests confirm the possibility of a stroke. In other embodiments, the device 20 automatically makes contact with a remote recipient, such as a health monitoring center, if the tests confirm the possibility of a stroke.

Stroke detection device 20 includes a controller 22, a memory 24, one or more cameras or image sensors 26, one or more accelerometers 28, a display 30, a cellular network transceiver 32, a WiFi transceiver 34, a USB port 36, a microphone jack 38, and a microphone 40. Stroke detection device 20 also optionally includes a Subscriber Identity Module (SIM) card 42. SIM card 42 is present in those embodiments of stroke detection device 20 that communicate with a cell phone network using Global System for Mobiles (GSM) technology. Stroke detection device 20, however, can also be implemented on a cell phone that uses Code Division Multiple Access (CDMA) technology, in which case it is not necessary to include a SIM card 42. The optional nature of SIM card 42 is represented in FIG. 1 by the dashed lines.

In the embodiment shown in FIG. 1, controller 22 is a conventional microcontroller that is found inside of a conventional cell phone that runs the electronics of the cell phone, as well as any apps that may have been downloaded to the cell phone. In other embodiments where stroke detection device 20 is not a cell phone, controller 22 may take on other forms besides that of a conventional microcontroller. In such embodiments, controller 22 may include any one or more microprocessors, microcontrollers, field programmable gate arrays, systems on a chip, volatile or nonvolatile memory, discrete circuitry, and/or other hardware, software, or firmware that is capable of carrying out the functions described herein, as would be known to one of ordinary skill in the art. Such components can be physically configured in any suitable manner, such as by mounting them to one or more circuit boards, or arranging them in other manners, whether combined into a single unit or distributed across multiple units.

Memory 24 is a non-volatile memory that stores one or more apps, the operating system of the device 20, the instructions executed by controller 22 in carrying out its cell phone functions, and one or more files containing data used by controller 22 when executing the stored apps. When stroke detection device 20 is implemented on an Android-based cell phone, memory 24 includes the Android operating system. When stroke detection device 20 is implemented on an Apple iPhone, memory 24 includes Apple's iOS operating system. In still other embodiments, stroke detection device 20 is implemented on a cell phone or other mobile device that utilizes another type of operating system besides Android and iOS (such as, but not limited to, Firefox OS, Sailfish OS, Windows Phone, Blackberry, Tizen, and others).

Regardless of the particular mobile operating system used with stroke detection device 20, memory 24 also includes a stroke detection app 44 that is executed by controller 22. Stroke detection app 44 carries out the stroke detection functions mentioned above, and described in more detail below, and effectively converts a conventional cell phone (or other mobile device) into a stroke detection device in accordance with one embodiment of the present disclosure.

Camera 26, accelerometer 28, display 30, cellular transceiver 32, and WiFi transceiver 34 are all conventional components that are built into the cell phone in a conventional manner. Accelerometer 28 is used by the controller 22 to automatically change the orientation of images displayed on display 30, as well as for other purposes when controller 22 executes stroke detection app 44. Accelerometer 28 is a three axis accelerometer capable of measuring acceleration in three orthogonal directions. Accelerometer 28 can be replaced in some embodiments by three single axis accelerometers that are each oriented so as to measure acceleration in three orthogonal directions.

Display 30 is a conventional touch screen display, or other type of display, used on conventional cell phones. Cellular transceiver 32 is a conventional transceiver used by the cell phone to communicate with one or more cell towers of a cellular network, thereby enabling the cell phone to communicate via telephony. WiFi transceiver 34 is a conventional transceiver (e.g. IEEE 802.11) that enables the cell phone to communicate with one or more wireless access points of a computer network that is within range of the cell phone and that is WiFi-enabled. WiFi transceiver 34, like SIM card 42, is an optional component that need not be present on the cell phone in order for stroke detection app 44 to operate. The optional nature of WiFi transceiver 34 is represented in FIG. 1 by the dashed lines.

In some embodiments of stroke detection device 20, more than one camera 26 is included. For example, in many embodiments, stroke detection device 20 includes a user-facing camera 26 and an away-facing camera 26. The use of these two types of cameras is common on many cell phones. The user-facing camera 26 faces toward the user when he or she is looking at the display 30 on the cell phone. The away-facing camera 26 is positioned on the opposite side of the cell phone and faces the opposite direction as the user-facing camera. Stroke detection app 44 can be modified for use with cell phones having only a single camera 26, as well as cell phones that include more than one camera 26.

Stroke detection app 44 is configured to passively monitor one or more characteristics of the user of stroke detection device 20 and determine if those one or more characteristics show signs of a potential stroke. Specifically, it is adapted to passively monitor the user's facial features 46, speech 48, and gait 50. If the monitoring of any of these characteristics detects a sign of a stroke, stroke detection app 44 is configured to notify the user aurally and/or via display 30. In most cases, the notification is followed by instructions issued on display 30 requesting that the user performs additional tests, such as one or more of the FAST (face, arm, speech, and time) tests advocated by many professional health organizations, such as the American Stroke Association. The tests are performed using the stroke detection device 20 itself, thereby avoiding the need for a second person to be present. If the results suggest the possibility of a stroke, stroke detection device 20 informs the user and, in at least some embodiments, automatically contacts a stroke monitoring center or another predefined recipient.

As noted, the monitoring performed by stroke detection device 20 is passive. This means that stroke detection app 44, once downloaded onto stroke detection device 20, is programmed to automatically execute the monitoring of the person's facial features 46, speech 48, and gait 50 without requiring user intervention. Further, such monitoring occurs without interrupting the other functions performed by the stroke detection device 20 (e.g. making/receiving telephone calls, texting, surfing the Internet, etc.) and without interfering with any one or more other apps 52 that may be present in memory 24 and being executed by controller 22. Still further, in at least one embodiment, the monitoring of the person's gait 50 continues to take place when the user has turned off the illumination of display 30, as well as when the user has placed the cell phone into the airplane mode (i.e. when communications with the cell phone network are temporarily suspended by the user).

When stroke detection app 44 is initially downloaded to stroke detection device 20, controller 22 presents one or more screens on display 30 requesting that the user enter a plurality of baseline characteristics that will subsequently be used by controller 22. These baseline characteristics include a photograph of the user, a speech sample of the user, and a gait sample of the user. Once these baseline samples are collected, stroke detection app 44 stores them in one or more files in memory 24 and compares them with subsequently gathered images, speech samples, and/or gait samples that are gathered by camera 26, microphone 40, and accelerometer 28, respectively. If the comparison of any of these subsequently gathered samples with their corresponding baseline samples differs by more than corresponding pre-defined thresholds, then stroke detection device 20 determines that a stroke may have taken place and issues a notification to the user.

Turning specifically to the baseline user images gathered during the set-up of stroke detection device 20, controller 22 displays a request on display 30 that the user take a photograph of his or her face using camera 26. The request further specifies that the user assume a specific expression, such as a smile or one with straight lips (no smile or frown). In one embodiment, controller 22 requests that the user take multiple photographs of his or her own face using camera 26 that are each of different facial expressions. After the photos are taken, controller 22 allows the user to identify to stroke detection app 44 which photos correspond to which expressions. Controller 22 then stores these images as baseline images for that particular user in memory 24.

After the baseline images are captured, stroke detection app 44 is configured to automatically analyze all subsequent photos taken by camera 26 to determine if the user is present in the photos. This is accomplished using conventional facial recognition software and the baseline image(s) of the users face stored in memory. When controller 22 detects that a photo has been taken with camera 26 that includes the user, controller 22 further analyzes those pixels of the photo corresponding to the users face. More specifically, controller 22 analyzes the facial pixels to determine if there is any facial droop present in the current image of the person's face and, if so, to further determine if the facial droop is greater than what is present in the user's baseline image. That is, controller 22 analyzes both the right half and the left half of the user's face and determines if one or more of the right facial features are asymmetric with their corresponding left facial features. Such facial features include the users mouth and eyes.

When analyzing the users mouth, controller 22 compares the relative distance that the right and left corners of the users lips extend upward or downward on the person's face. If controller 22 detects that the right and left lip corners do not extend upward or downward on the users face a substantially equal distance, controller 22 consults the baseline image of the person's face. That is, for example, if the user's left lip corner is higher on the person's face that his or her right lip corner, or the person's right lip corner is lower on his or her face than his or her left lip corner, controller 22 consults the baseline image of the person's face. From the baseline image, controller 22 determines if the asymmetry in the user lips from the current image of the user is more than any asymmetry that may have been present in the baseline image. In other words, controller 22 determines if any asymmetry in the users lips is greater than what may be a normal amount of asymmetry for that person. When making this comparison, controller 22 classifies the user's facial expression in the current image (e.g. smiling, frowning, straight, open mouth, or other) and uses the corresponding baseline image (if more than one) for comparison purposes.

When analyzing the user's eyes, the controller 22 uses a similar method. That is, controller 22 determines the relative amount of upward or downward distance of the users right and left eye brows and/or right and left eyelids. If controller 22 detects that the right and left eye brows or right and left eyelids do not extend upward or downward on the user's face a substantially equal distance, controller 22 consults the baseline image of the person's face. From the baseline image, controller 22 determines if the asymmetry in the user's eye brows or eye lids, as shown in the current image of the user, is more than any asymmetry that may have been present in the baseline image. When making this comparison, controller 22 may classify the users facial expression in the current image (e.g. smiling, frowning, straight, open mouth, or other) and uses the corresponding baseline image (if more than one) for comparison purposes.

In other embodiments, stroke detection app 44 detects and compares still other facial features to determine if there is any abnormal asymmetry in the person's face. Such other features may include comparison of the users nose, hairline (if visible), ears, and other features. In some case, stroke detection app 44 uses features that are unique to that particular individual, such as scars, moles, birthmarks, etc. when looking for asymmetrical changes in the user's face.

When stroke detection app 44 detects an asymmetry in any one or more of the user's facial features, it is programmed in at least one embodiment to automatically issue a notification to the user, along with instructions for taking one or more additional tests. The number of facial features in which asymmetry must be detected before stroke detection app 44 notifies the user and requests the user to take additional tests can be varied in different embodiments. Further, the degree by which the facial feature's asymmetry must vary from the baseline image before stroke detection app 44 notifies the user and requests the additional test can also be varied. In at least one embodiment, such variance is partially based upon health information input into memory 24 by the user and/or by additional information coming from one or more other sensors that are monitoring other characteristics of the user. In other words, if the user is at risk for a stroke (e.g. has diabetes or high blood pressure), the variance necessary to trigger notification and additional tests may be smaller than for users who do not have such risk factors. Similarly, if there is additional sensor information being forwarded to controller 22 (as discussed more below) that may suggest the possibility of a stroke, the variance necessary to trigger the notification and additional tests may be less than in the absence of that additional information.

In addition to automatically analyzing pictures taken by the user of stroke detection device 20 using camera 26, stroke detection app 44 is also configured to instruct controller 22, in at least one embodiment, to automatically use camera 26 to take one or more pictures of the user. In this embodiment, controller 22 analyzes not only images from camera 26 that are the result of the user manually using camera 26 to take photos, but also images from camera 26 that are gathered automatically without any user input. In such an embodiment, stroke detection app 44 instructs controller 22 to activate camera 26 at times when the user is utilizing the keyboard on stroke detection device 20 (whether virtual or physical). In those instances, the stroke detection device is most likely to be naturally held by the user in an orientation where the user-facing camera 26 is aimed toward the users face. Accordingly, when controller 22 detects the usage of the keyboard, it instructs camera 26 to capture one or more images of the user and analyze them in the manners discussed above.

Further, in those embodiments where controller 22 automatically captures images of the user, controller 22 may be adapted to automatically capture video sequences of the user. By capturing video images, rather than single still images, controller 22 is able to process multiple images in its search for facial droop, which may provide better reliability due to the fact that some images may not have been captured while the camera 26 was aimed precisely right, or may have been captured in manners that provide less useful images for facial droop analysis.

Regardless of whether or not camera 26 automatically or manually captures images of the user and/or whether it automatically captures video sequences, rather than still images, the captured images may yield varying results in terms of the usefulness in detecting facial droop. That is, depending upon the angle of the person's face in the photo, the size, the lighting, and other factors, certain captured images may not be as useful for detecting facial droop as others. In at least one embodiment, controller 22 analyzes these factors (angle, lighting, size, etc.) and generates an estimate of the usefulness of the photo in detecting facial droop. This estimate is used by controller 22 when determining whether to issue an alert to the user and/or take additional tests. That is, the lower the estimate, the less likely an alert will be issued based off of an image analysis that detects a small amount of facial asymmetry.

In addition to, or alternatively to, the automatic capturing of images of the user's face when he or she is using the keyboard on stroke detection device 20, stroke detection app 44 may be configured to instruct controller 22 to automatically capture images of the users face at other times. As one such example, controller 22 may be instructed to capture images of the user when the user is engaged in a video call (e.g. using a service such as Skype®, Facetime®, or the like). When so configured, controller 22 both transmits the captured images to the other participants in the video call and analyzes the images for facial droop. Controller 22 thus processes the captured images in at least two different manners.

Facial images may also be automatically gathered by stroke detection app 44 at still other times. Such additional times may include, depending upon the particular manner in which stroke detection app 44 is programmed, times when the user is utilizing the away-facing camera 26 to take pictures. In such embodiments, controller 22 automatically uses user-facing camera 26 to capture one or more images of the user while the user is using the away-facing camera 26 to take pictures. The captured images are analyzed in the manner discussed above. Stroke detection app 44 can be configured to automatically capture facial images of the user in still other situations.

As was mentioned previously, stroke detection device 20 is also configured to passively monitor a users speech 48. In at least one embodiment, when stroke detection app 44 is initially downloaded to stroke detection device 20, controller 22 presents one or more screens on display 30 requesting that the user enter one or more baseline voice samples that will subsequently be used by controller 22. These baseline samples include the user speaking words and phrases into microphone 40. Once these baseline sound samples are collected, stroke detection app 44 stores them in memory 24 and compares them with subsequently gathered sound samples from the user. As with the images captured from camera 26, if the comparison of any of these subsequently gathered sound samples with their corresponding baseline sound samples differs by more than corresponding predefined thresholds, then stroke detection device 20 determines that a stroke may have taken place and issues a notification to the user.

Turning specifically to the baseline voice samples gathered during the set-up of stroke detection device 20, controller 22 displays a request on display 30 that the user read one or more sentences that are displayed on display 30. While the user reads these sentences, controller 22 captures the users voice via microphone 40 and correlates the sounds emitted by the person with the specific words in the sentences. In some embodiments, stroke detection app 44 is configured to request that the user speak into microphone 40 the phrase or greeting commonly used by that particular user when answering a phone call. Using conventional speech-to-text software that is included as part of stroke detection app 44, controller 22 displays the text corresponding to the users phrase or greeting and asks the user to confirm and/or correct the text. In this manner, a baseline voice sample is gathered of that particular users voice that corresponds to that user's customary phrase when answering a voice call. Other types of voice samples may also be gathered and stored in memory 24.

After the baseline sound samples are captured, stroke detection app 44 is configured to automatically analyze all subsequent voice samples from the user that are captured by microphone 40 to determine if the user may have experienced a stroke. This is accomplished by comparing characteristics of the current sound samples with corresponding characteristics of the baseline samples. Such characteristics include speed, volume, pitch, emphasis, and pronunciation (including the dropping of syllables or whole words in phrases), as well as any other speech characteristics that can be measured and that may be indicative of a changed speech pattern.

Stroke detection device 20 is adapted to gather sound samples from the user during the user's normal usage of the stroke detection device 20. That is, controller 22 gathers sound samples when the user is speaking during a phone call (or video call), as well as when the user is using the voice command or dictation features of the cell phone (if the cell phone is so equipped). Controller 22 determines the words and/or phrases being spoken by the user in the current sound samples and compares those words and/or phrases to baseline samples of the same words and/or phrases. Specifically, controller 22 compares one or more of the speed, volume, pitch, emphasis, and pronunciation of the current sound samples with those of the baseline samples. In at least one embodiment, controller 22 executes an algorithm where it assigns each of these speech characteristics (speed, volume, etc.) a numeric level of importance, and the magnitude of the differences in that characteristic from the baseline characteristics are multiplied by the numeric level of importance. This is done for each characteristic. The products of the multiplication of each characteristic are then summed together and, if they exceed a predetermined threshold (which may be individually tailored to a particular user based on an assessment of that person's risk factors for stroke), controller 22 issues an alert to the user and requests that the user take one or more additional tests.

In at least one alternative embodiment, controller 22 is programmed so that no manually recorded baseline samples of the users voice are necessary. When so programmed, controller 22 automatically builds up baseline samples of the users voice in memory 24 during the user's normal usage of the cell phone (e.g. speaking during phone calls, etc.). Controller 22 uses speech-to-text technology to recognize the words spoken by the user and store the sound samples in memory 24 according to the spoken words and/or phrases. In some cases, multiple baseline sound samples may be taken for the same word or phrase. In this manner, averages of the user's voice characteristics can be taken, thereby establishing an acceptable range of deviation of the various voice characteristics when the user speaks each word or phrase. Utilizing these automatically gathered baseline sound samples (whether they include only a single baseline sound sample for a given word or a given phrase, or whether they include multiple sound samples for a given word or phrase), controller 22 compares the current sound samples to the corresponding baseline sound samples and issues an alert if the various characteristics differ by more than an acceptable amount.

Stroke detection device 20 is also configured to passively monitor a users gait 50. In at least one embodiment, when stroke detection app 44 is initially downloaded to stroke detection device 20, controller 22 presents one or more screens on display 30 requesting that the user place the cell phone in his or her pocket, or whatever other location he or she conventionally stores the cell phone while walking. Controller 22 further requests that the user take a specified number of steps at a normal walking pace. During those steps, controller 22 collects the outputs from accelerometers 28 and stores this data as a baseline gait reading that corresponds to the cell phone being in the stored position. Controller 22 also requests that the user take a specified number of steps at a normal walking pace while holding the phone to his or her head in the position he or she normally holds a cell phone while engaged in a phone call. During those steps, controller 22 also collects the outputs from accelerometers 28 and stores this data as a baseline gait reading corresponding to the phone being in the use position. In some embodiments, still other baseline gait readings are taken.

After the baseline gait readings are initially taken, controller 22 processes them to determine one or more baseline characteristics of the user's gait. The specific characteristics determined may vary from embodiment to embodiment. In at least one embodiment, controller 22 determines how much difference normally exists in the amount of motion sensed by accelerometer 28 between successive steps taken by the user. This provides an indication of how even or uneven the use's baseline gait is. In other words, controller 22 operates under the presumption that the user alternates feet when taking successive steps. Controller 22 therefore compares the accelerations (and/or displacement) sensed in every other step (e.g. the $1^{st}$, $3^{rd}$, $5^{th}$ steps, etc.) with the accelerations (and/or displacement) sensed in the steps between these (e.g. the $2^{nd}$, $4^{th}$, $6^{th}$, steps, etc.) and determines a baseline difference between successive steps. In other embodiments, controller 22 additionally or alternatively determines other characteristics of the users gait.

After the baseline gait readings are taken, processed, and stored, controller 22 takes additional readings from accelerometer 28 to determine the person's current gait. In some embodiments, these additional readings are taken substantially continuously, or at frequent periods, and then first analyzed to determine if they correspond to time periods when the user is walking or time periods when the user is stationary. If they correspond to time periods when the user is walking, controller 22 processes these readings in a similar manner as it processed the baseline readings and compares the processed results to the processed baseline reading results to determine if the user's gait has changed. The processed results include, in at least one embodiment, the speed of the user's walk. The processed results also include a comparison of the amount of acceleration (or displacement) sensed by the accelerometer between successive steps, as mentioned above (i.e. comparing accelerations (or displacements) of the even numbered steps with accelerations (or displacements) of the odd numbered steps, where the terms "even" and "odd" may be assigned based upon the first step detected in a particular sample). If controller 22 detects a significant change between one or more characteristics of the current gait sample and one or more corresponding characteristics of the baseline gait sample, controller 22 issues an alert. In assessing the significance of the change, controller 22, in one embodiment, includes a predefined numerical threshold that is used to gauge the measured difference in the current and baseline gait samples.

As with the speech and facial feature analyses performed by controller 22 and described above, the thresholds used by controller 22 when determining whether a gait change is of sufficient size to trigger an alert, the thresholds used by controller 22 may be individually tailored to the particular user based upon his or her health history, and in particular based upon medical conditions that the user may or may not have that are risk factors for stroke.

As noted above, when controller 22 detects the possibility of a stroke from any of its repetitive analyses of the user's facial features 46, speech 48, or gait 50, this triggers an alert to the user and instructions requesting the user to take additional tests. In some embodiments, stroke detection device 20 is configured to initiate the additional test in response to other triggers besides the analysis of the user's facial features 46, speech, or gait, as will be discussed in greater detail below. In still other embodiments, stroke detection device 20 may not monitor all three of the user's facial features 46, speech 48, and gait 50. For example, in at least one modified embodiment, stroke detection device 20 does not include accelerometers and does not monitor the user's gait. In this embodiment, stroke detection device 20 may be implemented as a cell phone, or it may be alternatively implemented as a laptop computer or desktop computer in which no accelerometers are included, or in which the accelerometers—if included—are not used by stroke detection app 44 for monitoring the users gait. In such embodiments, stroke detection app 44 may be modified to be a conventional software application rather than a downloadable app for mobile devices.

Figure 2B:
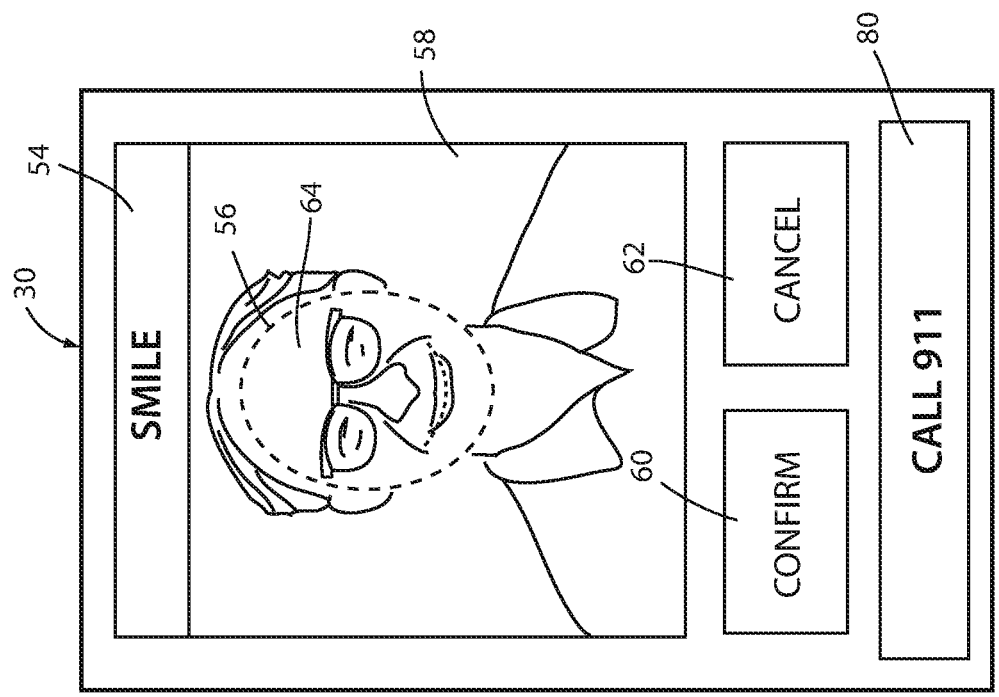
FIG. 2B is a second illustrative screen shot displayed on the stroke detection device of FIG. 1 when testing for facial droop in the user.
Figure 2A:
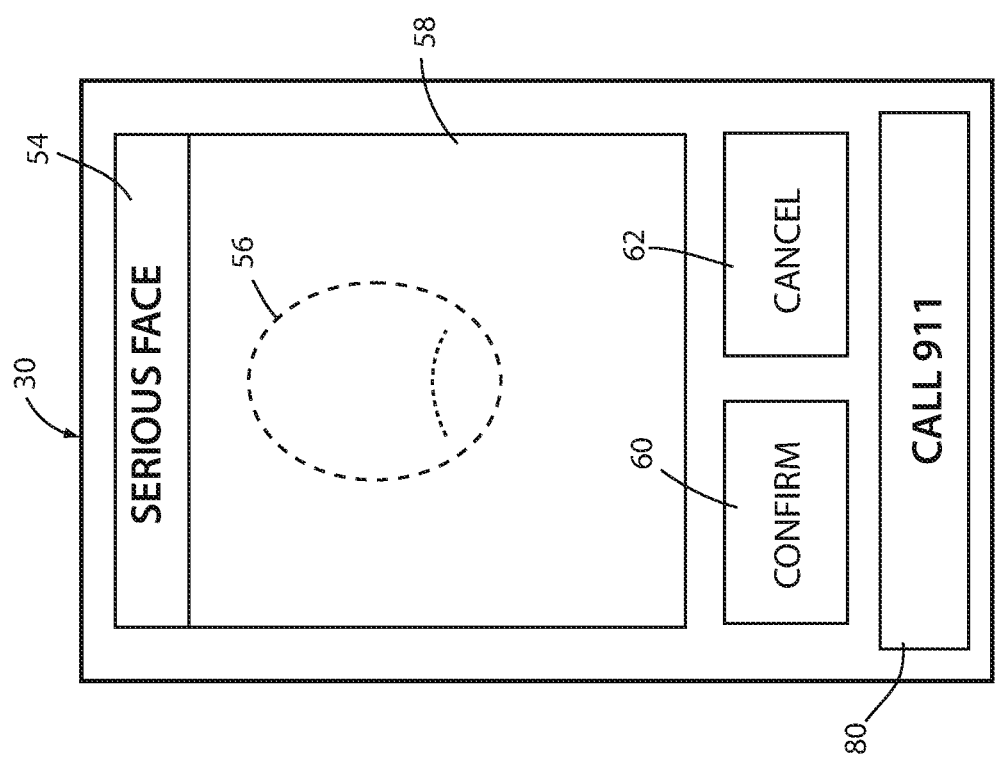
FIG. 2A is a first illustrative screen shot displayed on the stroke detection device of FIG. 1 when testing for facial droop in the user.
Figure 3:
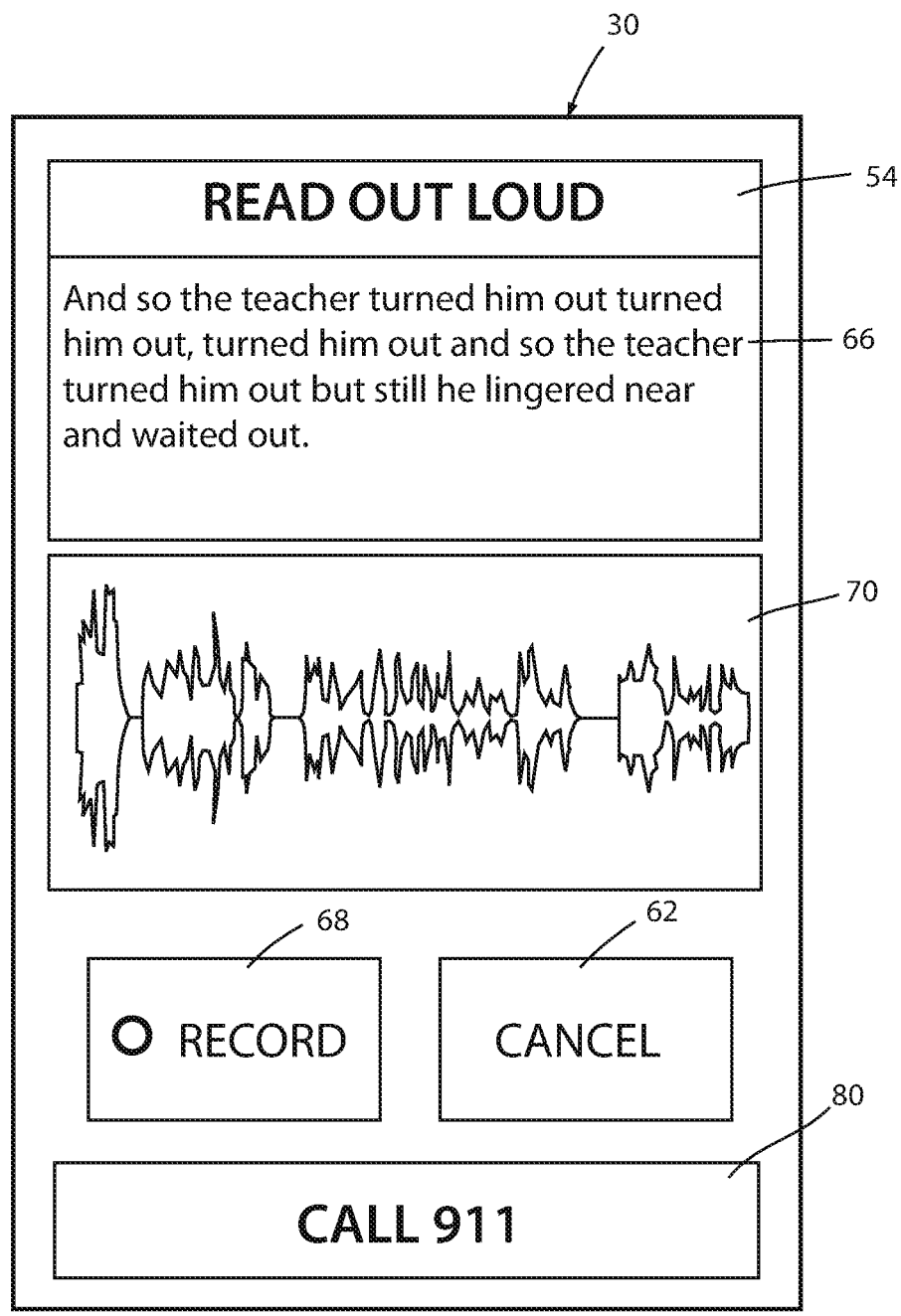
FIG. 3 is a third illustrative screen shot displayed on the stroke detection device of FIG. 1 when testing the speech of the user.
Figure 4B:
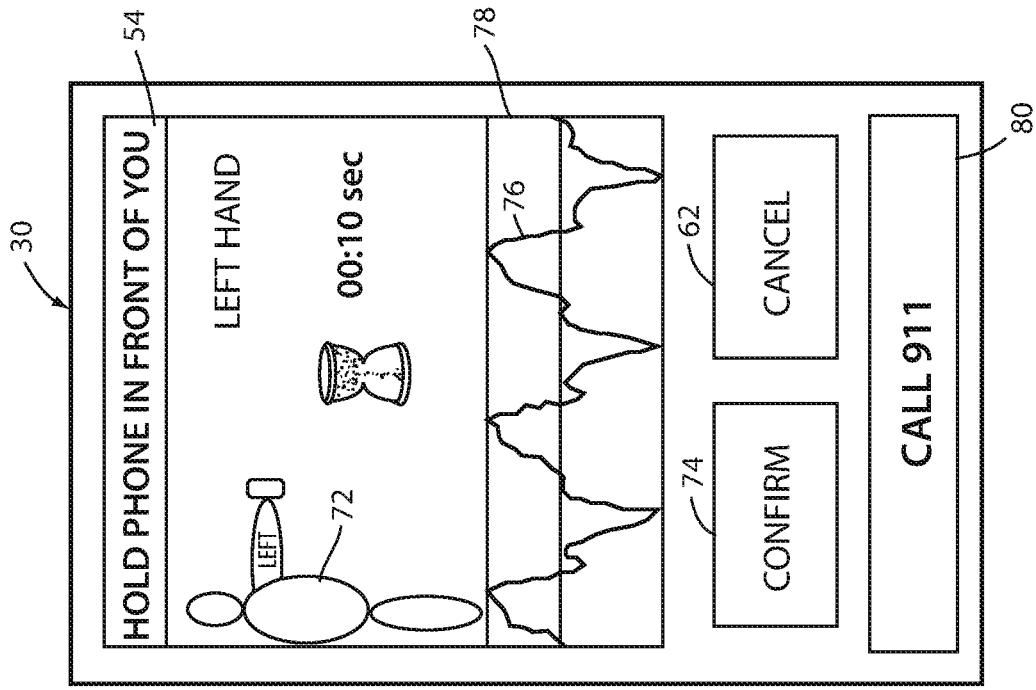
FIG. 4B is a fifth illustrative screen shot displayed on the stroke detection device of FIG. 1 when testing the steadiness of the users left arm and hand.

Regardless of the specific events that trigger stroke detection device 20 to instruct the user to take additional tests, FIGS. 2A-4B illustrate in greater detail the additional tests the user is requested to take. More specifically, FIGS. 2A-2B illustrate a test used to detect facial droop. FIG. 3 illustrates a speech test used to detect changes in the person's speech, and FIGS. 4A-4B illustrate a test used to detect the steadiness or lack of steadiness in the users arms. In some embodiments, stroke detection device 20 request that the user perform all three of these tests. In other embodiments, stroke detection device 20 requests that the user perform fewer than all three. In those embodiments where the user is requested to perform all three tests, the implementation of all three tests may provide additional or better information than what was obtained during the passive monitoring of the user. That is, for example, if the trigger for stroke detection device 20 requesting the tests was the possible detection of facial droop in a photograph of the user taken by camera 26, the implementation of the facial droop test shown in FIGS. 2A and 2B is still useful because the test of FIGS. 2A and 2B may be more accurate than passive monitoring of facial droop. Similarly, the speech test illustrated in FIG. 3 may be more accurate than the passive speech monitoring that occurs substantially continuously, or periodically, while the user is making normal use of his or her cell phone. These tests will now be described in greater detail.

Turning first to FIGS. 2A-2B, controller 22 executes a facial droop test utilizing the instructions and information shown in FIGS. 2A-2B. More specifically, as shown in FIG. 2A, controller 22 displays an instruction 54 on display 30 instructing the user to take a picture of himself or herself using camera 26. In the example of FIG. 2A, instruction 54 instructs the user to take the picture while the user has a serious expression. Controller 22 further displays on display 30 a target outline 56 (shown in dashed lines in FIG. 2A) within a box 58. Target outline 56 is generally oval shaped and provides a guide for the user on where to position his or her head when taking the picture. That is, box 58 corresponds to an area of display 30 on which controller 22 displays the current images being detected, but not yet captured, by camera 26. When the user aims camera 26 (the user-facing camera 26 if there are multiple cameras) toward himself or herself, an image of the user's face will appear in box 58. As the user adjusts the orientation of the camera 26 and the zoom level, the position of the users head in box 58 will change accordingly. As part of the facial droop test of FIG. 2A, the user will adjust the zoom level and orientation of the camera 26 until his or her head is shown in box 58 positioned within target outline 56 and at a size generally equal to target outline 56.

Once the user has oriented camera 26 and adjusted the zoom level to place his or her head inside of the target outline 56, as well as assuming the expression of a serious face—as requested by instruction 54—the user then presses the appropriate button (or location on display 30) to cause camera 26 to capture the person's image. Controller 22 then switches from displaying the images currently detected by camera 26 to displaying the static image captured by the user. The user then presses a confirm button 60 on display 30 if the captured image meets the requested criteria (i.e. the user's head is generally aligned with, and of the same size as, target outline 56, and the user has the requested facial expression). If the captured image does not meet the requested criteria, or if the user is otherwise not pleased with the captured image, he or she presses a cancel button 62 and is given the opportunity to take another image of himself or herself in the manner described above.

After capturing the image of the user's serious face, controller 22 moves to displaying the instructions 54 shown in FIG. 2B, which requests that the user capture an image of himself or herself with a smiling expression. Thus, the steps undertaken by the user with respect to FIG. 2B are the same as those taken with respect to FIG. 2A, except they are done with the user smiling instead of having a serious expression. Because these steps have been described already, they need not be described again. It should be noted, however, that FIG. 2B, unlike FIG. 2A, shows an illustrative example of a user's smiling image 64 captured by camera 26. The captured image 64 of FIG. 2B illustrates the proper alignment and size of the users head with respect to target outline 56.

Once acceptable images of the user with both a smiling and serious expression have been captured, controller 22 compares the images in the manner described above to the baseline images of the user stored in memory 24 in which the user has the same expression. That is, controller 22 compares the current smiling image to the baselines smiling image and the current serious image to the baseline serious image, looking for any signs of facial droop that may be evidenced by the appearance of the users lips, eyes, and/or other features on the user's face. In at least one embodiment, controller 22 assigns a numeric score to the amount, if any, of facial droop detected via the analyses of the smiling and serious self-images of the user. Controller 22 then moves onto the speech test illustrated in FIG. 3.

When requesting that the user take the speech test, controller 22 displays on display 30 instructions, such as instruction 54 of FIG. 3, that request the user to read out loud a specific sentence or group of sentences. Specifically, as shown in FIG. 3, instruction 54 requests that the user read out loud a sentence 66. To complete the test, the user first presses a record button 68 displayed on display 30 that activates microphone 40. Once pressed, the user reads the sentence 66 while speaking into microphone 40. The acoustic waves detected by the microphone 40 as the user speaks are displayed in a box 70 of display 30 in the embodiment shown in FIG. 3. In other embodiments, the acoustic waves are not displayed. Once the user has finished reading sentence 66 into microphone 40, the user presses the record button 68 again to terminate the recording. If the user was not satisfied with the recording, or otherwise wishes to perform it again, he or she can press the cancel button 62 to retake the speech test.

Once the sound sample of the user reading sentence 66 has been recorded, controller 22 compares this sound sample to the baseline sound sample. In at least one embodiment, the baseline sound sample will be of the user reading the same exact sentence 66. Controller 22 determines whether any characteristics (e.g. speed, volume, pitch, emphasis, and/or pronunciation) of this recent sound sample differ from the corresponding characteristics of the baseline sound sample, as described previously. Further, as also noted previously, controller 22 is programmed in at least one embodiment to assign a numerical score to the differences for each characteristic, multiply that score by a weighting factor, and sum together all of the multiplication products to arrive at a single numeric score that provides an overall indication of how the user fared on the speech test.

Figure 4A:
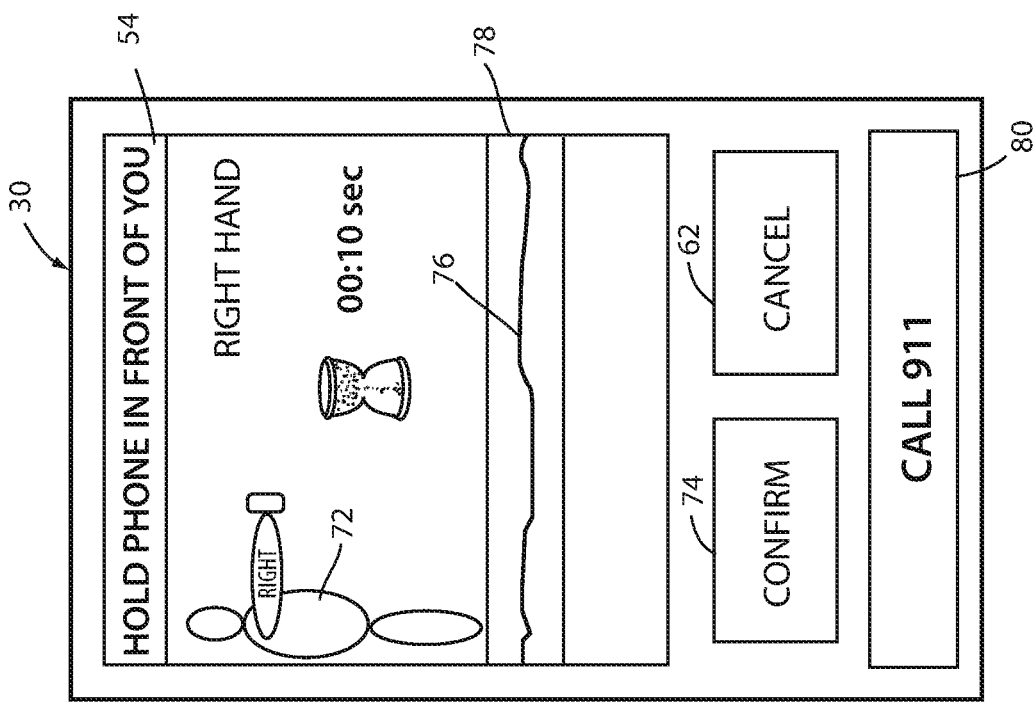
FIG. 4A is a fourth illustrative screen shot displayed on the stroke detection device of FIG. 1 when testing the steadiness of a user's right arm and hand.

After the speech test is finished, controller 22 requests that the user take an arm steadiness test. Illustrative screen shots that may be displayed on display 30 for implementing this arm steadiness test are shown in FIGS. 4A and 4B. The test begins with the screen shot shown in FIG. 4A in which the instruction 54 requests that the user attempt to hold his or her right arm out in front of himself or herself and steadily maintain it there for a set period of time (FIG. 4A illustrates a time period of 10 seconds, but this can of course be modified). In order to better assist the user, controller 22 displays on display 30 an icon 72 of a person holding the cell phone out in front of himself or herself with a straight arm. Once the user has the phone held out in front of himself in his or her right arm, the user presses a start button 74. Once the start button 74 is pressed, controller 22 records the outputs from accelerometer 28 for ten seconds (or other time period) while the user attempts to keep his or her right arm held out in a steady condition. After the set time period expires, controller 22 emits an aural and/or visual indication to the user that he or she may put his or her right arm down. If the user needs to perform the test again, or wants to cancel it midway through the test, he or she can press cancel button 62.

Once the user has successfully completed the right arm test of FIG. 4A, controller 22 switches to displaying images shown for the left arm test of FIG. 4B. The left arm test of FIG. 4B is the same as the right arm test of FIG. 4A except that the user switches from holding the cell phone with his right arm to holding the cell phone with his left arm, as indicated by the modified instruction 54 and modified icon 72. After the user had held the cell phone out in front of himself or herself for ten seconds in as steady as a manner as he or she can, controller 22 notifies the user, aurally and/or visually, that the test has ended. For both the right and left arm tests, controller 22 is programmed in the examples shown in FIGS. 4A and 4B to also display a graph 76 of the accelerometer data in a box 78. This, of course, can be omitted in other embodiments.

After accelerometer data from both the user's right arm and left arm has been collected by stroke detection device 20, controller 22 compares this data to the baseline readings stored in memory 24. Specifically, controller 22 compares the right arm accelerometer data to the baseline right arm accelerometer data and the left arm accelerometer data to the baseline left arm accelerometer data. After making these comparisons, controller 22 assigns a numeric score to the differences between the two right arm readings (current one and the baseline one) and also assigns a numeric score to the difference between the two left arm readings (current one and the baseline one). The differences may be quantified in a number of different manners, such as the sum of all of the acceleration samples, the sum of the displacements calculated from the acceleration samples, the number of changes in direction of the user's arm, and/or in other terms.

After stroke detection device 22 has executed all three of the droop, speech, and arm tests of FIGS. 2A-4B, controller 22 analyzes the scores from the respective tests and determines whether to recommend that the user seek prompt medical assistance or not. In at least one embodiment, this decision is independently made for each of the three tests. That is, if any one of the three tests shows a likelihood of a stroke, the user is urged to seek prompt medical assistance, even if the other two tests do not suggest the likelihood of a stroke. Indeed, in some embodiments, stroke detection device 20 is configured to analyze the results of each of the tests immediately after the test and determine then if the user should seek prompt medical assistance. In such embodiments, if the user performs poorly (i.e. in a manner suggestive of a stroke) on the first or second test taken, controller 22 instructs the user to seek prompt medical assistance immediately without waiting for the user to take the other remaining tests. This instruction may include both an audio indication as well as a visual indication on display 30.

As noted previously, the assessment of the test results is based upon comparing them to predetermined thresholds (for each test, or for each characteristic measured by the test) which may be individually tailored to the particular user. Thus, users with high stroke risk factors may be assigned lower thresholds than users with low stroke risk factors. The determination of those stroke risk factors is input into stroke detection device 20, in at least one embodiment, during its initial set up. More specifically, stroke detection app 44 is programmed to ask the user a series of questions when it is initially installed that relate to stroke risks. Such questions include questions regarding the users blood pressure, the absence or presence of diabetes, the occurrence of previous strokes, as well as any other questions that are relevant to assessing the user's risk for stroke.

It will be understood by those skilled in the art that, although the tests of FIGS. 2A-4B have been described as taking place in a particular order, this order has been selected merely for purposes of illustration. That is, the particular order in which the facial droop, speech, and arm tests are implemented can be varied.

As shown in FIGS. 2A-4B, controller 22 also displays on display 30 a "call 911" button 80 at the bottom of display 30 during each of the facial droop, speech, and arm tests. Button 80 allows the user to quickly call 911 at any time during the performance of these tests. In some embodiments, button 80 is supplemented with a "call Dr. X" button or a "call stroke monitoring center" button where "X" refers to the specific doctor or caregiver of the user. When supplemented with such buttons, the contact information for the particular doctor or monitoring center is input by the user during the initial set up of stroke detection app 44.

In some embodiments, stroke detection device 20 is programmed to automatically communicate with a remote recipient if any of the facial droop, arm, or speech tests indicate the possibility of a stroke. Such automatic communication can take on a variety of different forms and is configured by the user during the initial set up of stroke detection app 44. For example, in one embodiment, when stroke detection device 20 detects the possibility of a stroke, it may be configured by the user to automatically send a text, email, or other predefined message to a predesignated individual or individuals 82 (FIG. 1) that has been selected by the user. This automatic communication takes place either via WiFi transceiver 34 or via cellular transceiver 32, depending upon whether or not a WiFi connection or cellular connection is currently available. The predesignated individual(s) 82 may be a relative of the user, a caregiver of the user, or other individual. If stroke detection device 20 is configured to contact multiple predesignated individuals, multiple phone calls, texts, emails, or the like are transmitted by the cell phone to each of the predesignated individuals 82. The content of the phone call (which is either prerecorded or generated by a voice synthesizer), text, and/or emails is entered during the initial set up of stroke detection app 44. In some embodiments, the content of the phone call, text, or email will vary depending upon the circumstances triggering the call. For example, the content may indicate which ones of the facial droop, arm, and/or speech tests of FIGS. 2A-4B the user has taken, which ones are suggestive of a stroke, and/or other information. The designated recipients may then use that information to make a phone call to the user, or to instead directly contact a hospital 84 or a stroke monitoring center 86.

In some embodiments, when stroke detection device 20 detects the possibility of a stroke, it may be configured by the user to alternatively or additional automatically send a text, email, or other predefined message to stroke monitoring center 86 and/or to hospital 84. Such communication also takes place either via WiFi transceiver 34 or cellular transceiver 32, depending upon which is available. The particular hospital 84 or stroke monitoring center 86 which is automatically contacted, along with the contact information for the hospital 84 and/or monitoring center 86, is selected by the user during the initial set up of stroke detection app 44. As with the automatic communication that takes place when stroke detection device 20 automatically contacts one or more individuals 82, stroke detection device 20 can be configured by the user to forward a predetermined voice message (recorded or synthesized), a text, an email, or other type of communication to the hospital 84 and/or monitoring center 86. Whatever the type of communication, it may include data regarding the results of any one or more of the facial droop, arm, and/or speech tests taken by the user.

In addition to test data, the data forwarded to any of individuals 82, hospital 84 and/or monitoring center 86 includes data identifying the particular user. Particularly for communications with hospital 84 and/or monitoring center 86, the communication includes not only the name of the user, but also, in some instances, a patient code that uniquely identifies the patient with a code that is known to the hospital 84 or monitoring center 86. In other words, the hospital 84 or monitoring center 86 typically will include in their own records information about the user, such as his or her medical records and contact information, and this will often be assigned a code or other identifier by the hospital or monitoring center. By including this code or other identifier in the communication from stroke detection device 20, the hospital 84 or monitoring center 86 can automatically retrieve additional information about the user.

When contacting the monitoring center 86, personnel at the monitoring center 86 review the results of the tests taken with stroke detection device 20 (and communicated thereto) as well as the medical records of that particular user before determining whether to contact hospital 84. Such personnel may also or alternatively place a phone call to the user of stroke detection device 20 to gather more information about the user's current condition and/or to provide instructions to seek prompt medical assistance at a particular hospital 84. Other functions and tasks may also be carried out by the personnel of the monitoring center.

In at least one embodiment, the automatic communication of stroke detection device 20 with any of individuals 82, hospital 84 and/or monitoring center 86 also includes information about the current location of the user of stroke detection device 20. This location information is determined by a location app 88 that is included within memory 24 of stroke detection device 20. Location app 88 is a conventional location determining app that, in some embodiments, comes preinstalled on the cell phone when the user purchases the cell phone. Location app 88 may determine the users current location by using the location of the cell phone towers the phone is currently in communication with, or it may determine location based upon a GPS capability of the phone, or it may determine location based upon the WiFi wireless access points the phone is in communication with, or it may determine location based upon a combination of two or more of these methods. By automatically forwarding the current location of the user to one or more recipients (e.g. individual 82, hospital 84, and/or monitoring center 86), the recipient is able to summon an ambulance, or other rescue personnel, to the user should the condition of the user warrant such a step.

Figure 5:
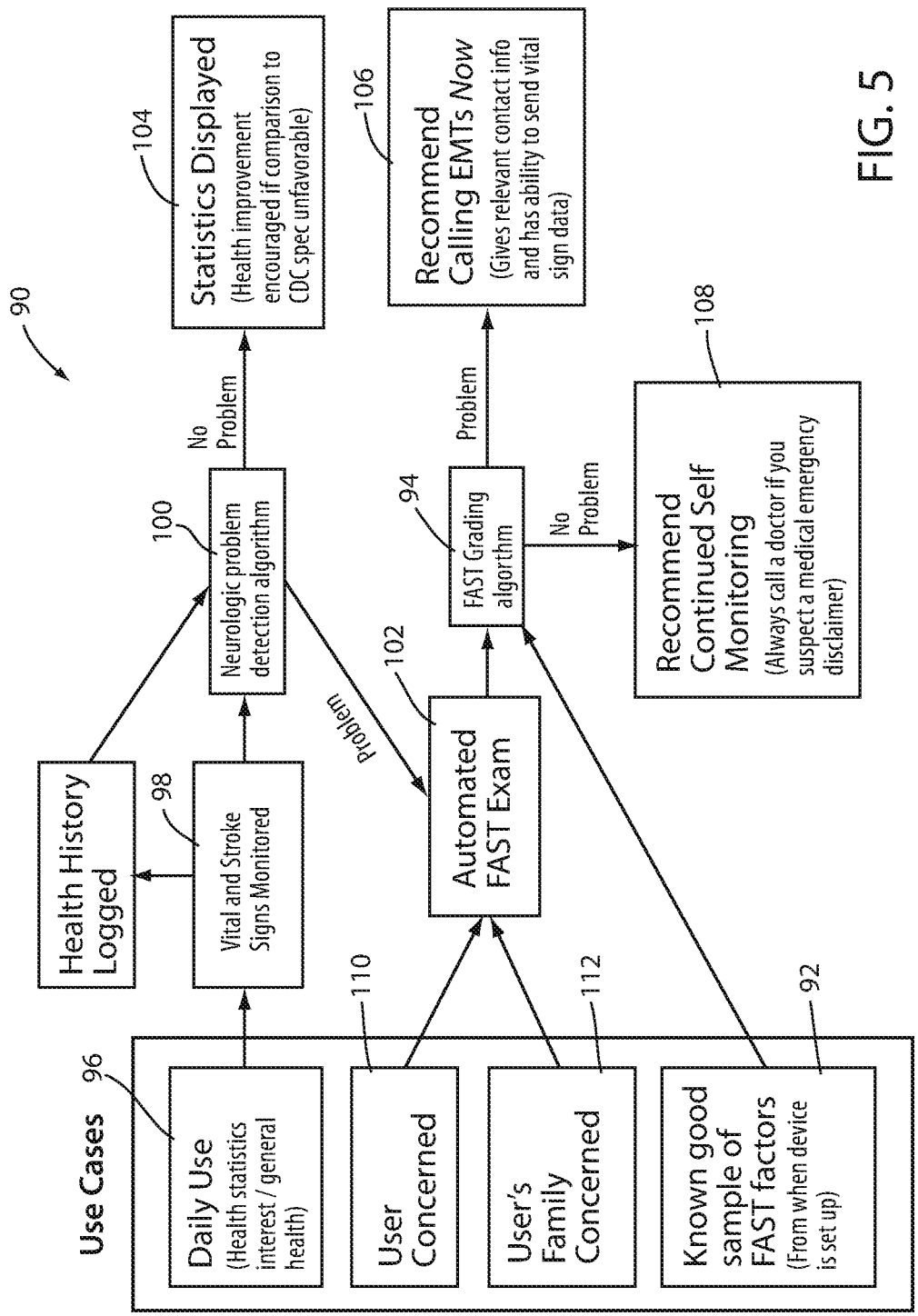
FIG. 5 is an flowchart of an illustrative algorithm that may be followed by the stroke detection device of FIG. 1.

FIG. 5 illustrates a stroke detection method 90 for utilizing stroke detection device 20. Stroke detection method 90 begins at a baseline entry step 92 where the user inputs baseline data for each of the facial droop, arm, and speech tests of FIGS. 2A-4B, in the manner discussed previously. That is, at step 92, the user takes one or more pictures of himself using stroke detection device 20 while assuming one or more specific expressions, inputs one or more sound samples of the user reading specific phrases or sentences, and holds his or her arms straight out while attempting to keep them steady for a predetermined time period. These baseline readings are stored in memory 24 and used when grading future test results of that user at a grading step 94.

After the user has entered baseline data at step 92, the use of stroke detection device 20 may commence in one of three different ways. The first is through daily use of stroke detection device 20, as indicated at step 96. When used daily, stroke detection device 20 automatically and passively monitors various characteristics of the user in the manners described above at a monitoring step 98. This includes, as noted, passively and automatically monitoring the user's speech, face, and/or gait while he or she makes normal use of the stroke detection device 20. In some embodiments not yet described, monitoring step 98 may also include the additional monitoring of one or more vital signs of the user.

The results of the passive monitoring that takes place at step 98 are analyzed at step 100 by controller 22 to determine if a stroke may have occurred. If the analysis suggests the possibility of a stroke, controller 22 proceeds to a testing step 102. If the analysis does not suggest the possibility of a stroke, controller 22 proceeds to a notification step 104 in which information about the analysis at step 100 is displayed to the user.

Test step 102 (FIG. 5) involves the user taking the tests previously described above with respect to FIGS. 2A-4B. The results of these tests are graded at grading step 94 in one or more of the manners previously described. If the grading suggests that a stroke may have occurred, the user is notified at step 106 and urged to seek prompt medical attention. Step 106 may also involve the automatic communication with one or more remote recipients (e.g. individual 82, hospital 84, and/or monitoring center 86), as was also previously described. If the grading does not suggest that a stroke occurred, controller 22 displays a different notification at step 108 that explains to the user that the tests were not indicative of a stroke, but that the user should seek prompt medical attention if the user does not feel normal or otherwise feels that medical attention is appropriate.

The use of stroke detection device 20 may alternatively commence in response to a concern of the user or a member of his or her family (or anyone else who is associated with the user). That is, if a user is concerned about his or her own current health status, he or she may manually prompt testing at step 110. Such prompting causes controller 22 to execute test step 102 in the manner previously described. If a member of the user's family is concerned, the family member may also manually commence testing at a step 112. This family member manual commencement causes controller 22 to execute test step 102 in the same manner as the users manual commencement does at step 110.

In some embodiments, stroke detection app 44 is configured to allow the family member to commence testing at step 112 remotely. Thus, for example, if the user of stroke detection device 20 is talking on the cell phone to a family member and his or her voice or behavior causes concern to the family member, the family member may remotely instruct stroke detection device 20 to commence testing. Such remote control may be implemented in a variety of manners. In one such manner, the family member dials a predetermined number during the phone conversation with the user of stroke detection device 20. This transmits a predetermined set of aural signals to the stroke detection device 20, which responds by commencing testing. In some embodiments, the commencement of the testing locks the user out from performing other functions with the cell phone (except contacting 911 or one of the recipients 82, 84, or 86) until the testing is complete, thereby encouraging the user to complete the testing.

Figure 6:
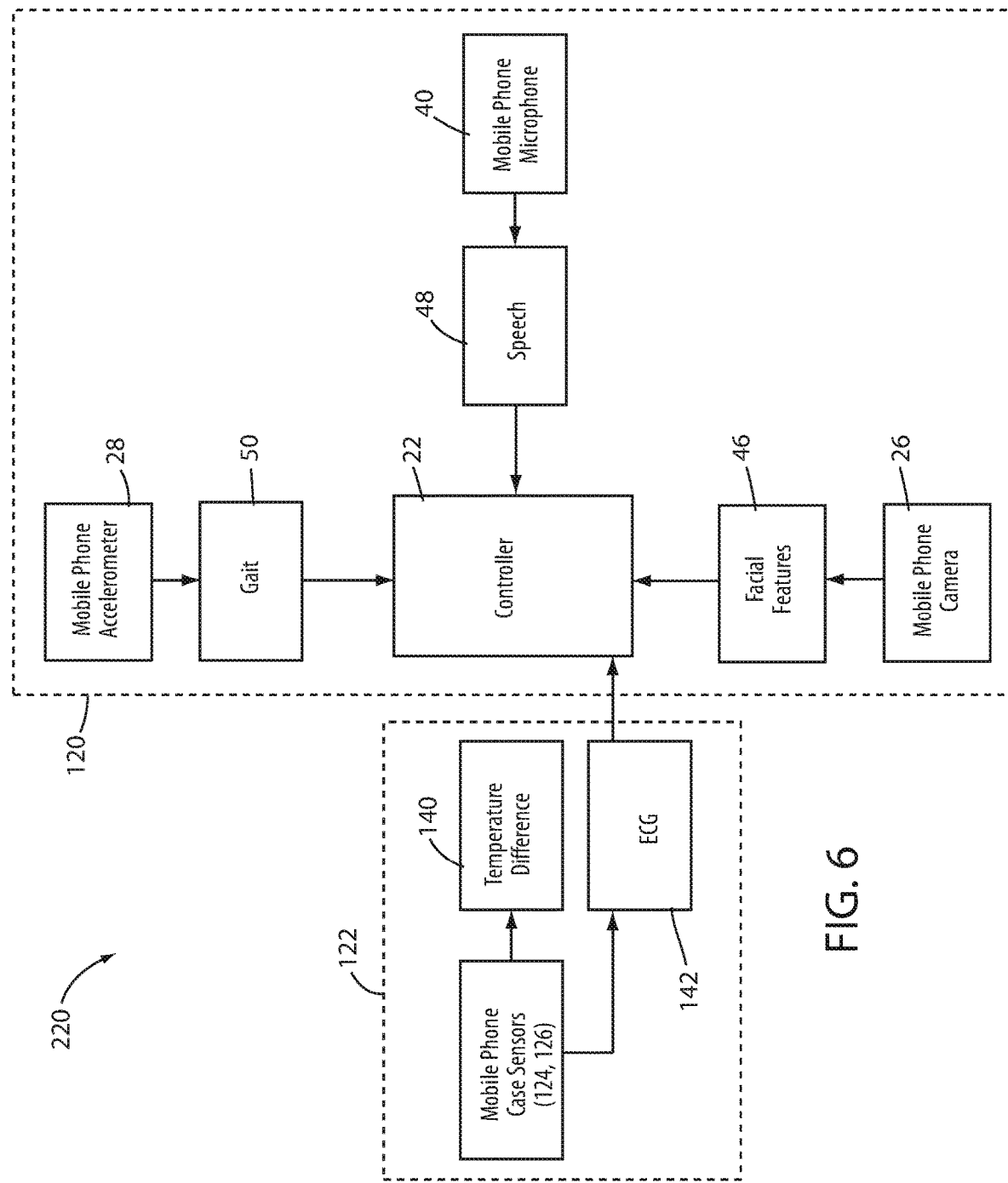
FIG. 6 is a block diagram of a second embodiment of a stroke detection device.

FIG. 6 illustrates an alternative embodiment of a stroke detection device 220 according to the present disclosure. Stroke detection device 220 includes a number of components in common with stroke detection device 20, as well as one or more components that are not found in stroke detection device. Those components that are the same as, and operate in the same manner as previously described, are labeled in stroke detection device 220 with the same reference numbers as were used with stroke detection device 20. Those components that are new are labeled with a new number, and those components that are similar, but modified in some way, bear the same reference number as found in stroke detection device 20 but increased by two hundred.

Stroke detection device 220 of FIG. 6 differs from stroke detection device 20 of FIG. 1 in a number of respects. One of these is the fact that stroke detection device 220 is comprised of two separate components: a main device 120 and an auxiliary device 122. In the particular embodiment of stroke detection device 220 shown in FIG. 6, main device 120 includes all of the same components that are found in stroke detection device 20 of FIG. 1. Indeed, in the embodiment of FIG. 6, main device 120 is a cell phone, just as stroke detection device 20 is shown in FIG. 1 to be a cell phone (although it may be implemented in other forms). Although FIG. 6 does not show main device 120 as including every single component of stroke detection device 20, this has been done for purposes of avoiding clutter in FIG. 6 in order to better clarify this particular embodiment. It will therefore be understood that, although not shown in FIG. 6, main device 120 includes, in addition to the components shown in FIG. 6, a memory 24, a display 30, a USB port 36, a cellular transceiver 32, a microphone jack 38, and, in some embodiments, one or both of a WiFi transceiver 34 and SIM card 42. Although also not shown in FIG. 6 for purposes of clarity, main device 120 is capable of communicating with one or more designated individuals 82, hospitals 84, and/or monitoring centers 86, in any of the manners previously described.

The memory 24 of main device 120 includes a stroke detection app that includes all of the features and functions of stroke detection app 44, but that has been modified to work in conjunction with auxiliary device 122, as will be described in greater detail below. Main device 120 therefore can be operated in accordance with method 90, as described above.

Figure 7:
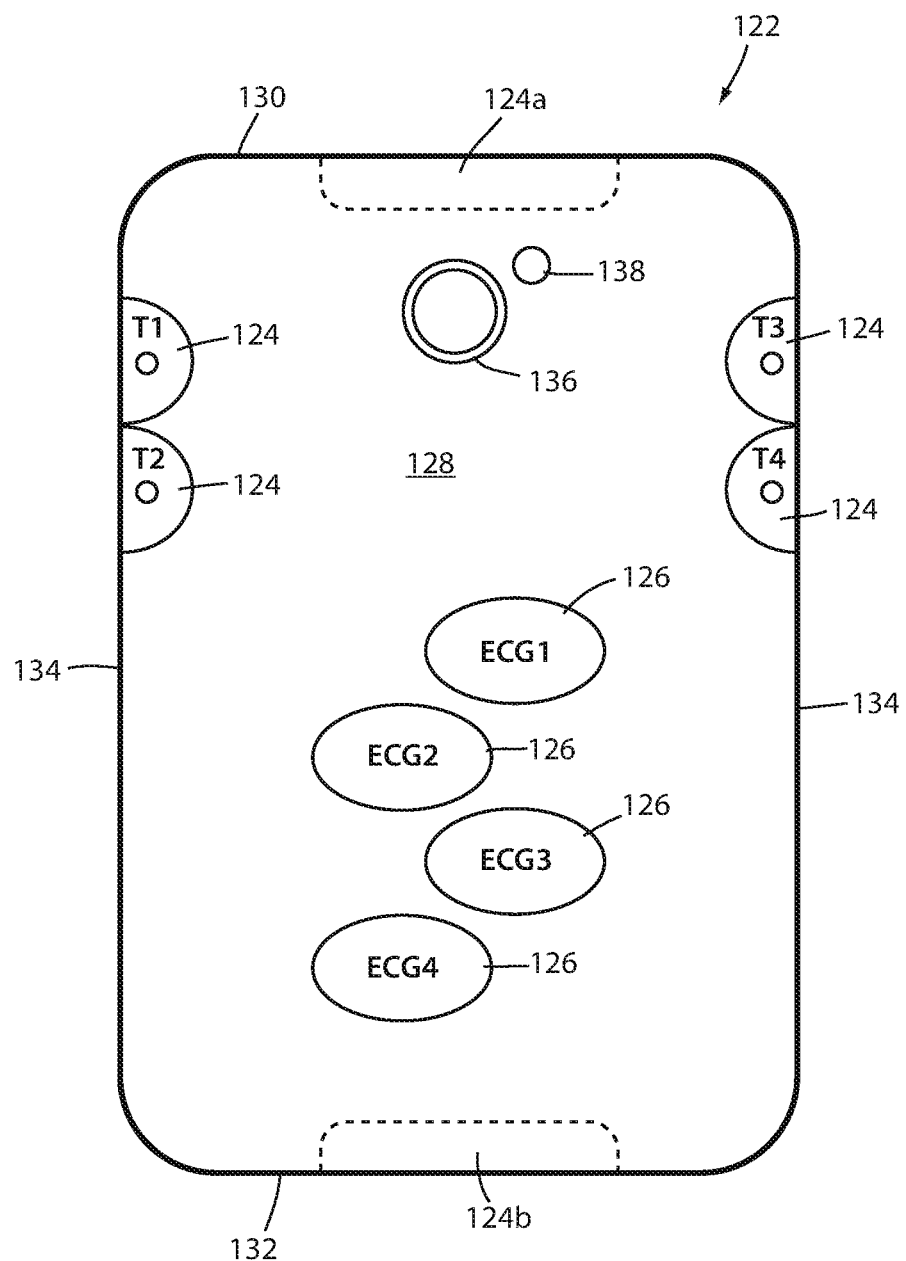
FIG. 7 is rear elevation view of a cell phone case usable in the stroke detection device of FIG. 6.

Auxiliary device 122 of stroke detection device 220 is adapted to provide additional information to controller 22 regarding the stroke risk and/or the possibility of the user of device 220 having experienced a stroke. Specifically, auxiliary device 122 of stroke detection device 220 is adapted to detect temperature differences 140 between the right and left sides of the users body, as well as ECG readings 142 from the user. Although auxiliary device 122 can take on a variety of different forms, some of which will be described in greater detail below, auxiliary device 122 is shown in FIG. 6 to specifically be a cell phone case that fits over, and attaches to, main device 120. As shown in FIG. 7, auxiliary device 122 includes a plurality of temperature sensors 124 and a plurality of electrocardiography (ECG) electrodes 126. Sensors 124 and electrodes 126 are defined on a back face 128 of auxiliary device 122. Back face 128 faces away from the user of stroke detection device 220 when the user is holding device 220 such that display 30 is facing the user. Back face 128 includes a top 130, a bottom 132, and a pair of side 134. Back face 128 further includes a first aperture 136 positioned to align with camera 26 of main device 120 when auxiliary device 122 is coupled to main device 120. Back face 128 further includes a second aperture 138 positioned to align with a light coupled to main device 120 that is used for flash photography and/or for other purposes.

Auxiliary device 122 can be used in conjunction with main device 120 in one of two different manners. In a first embodiment described immediately below, auxiliary device 122 is only used to provide additional information about the user prior to making a determination about whether the user should seek immediate medical treatment or not, and is not used to trigger testing step 102 of method 90. In a second embodiment that is described thereafter, auxiliary device 122 is used as an additional tool for passively monitoring temperature characteristics of the user and will trigger testing step 102 if the passive monitoring yields data indicative of the possibility of a stroke.

Turning to the first embodiment, controller 22 of main device 120 is configured in stroke detection device 220 to also request as part of step 102 that the user utilize sensors 124 and electrodes 126 to take temperature readings and ECG readings of the user. These requests can occur before, after, or during the facial droop, arm, and speech tests of FIGS. 2A-4B. When requesting a temperature reading from the user, controller 22 displays instructions on display 30 of main device 120 requesting that the user position one or more of his or her right fingers on the temperature sensors 124 that are located on a first one of the sides 134 of auxiliary device 122, and that the user also positions one or more of his or her left fingers on the temperature sensors 124 that are located on the second and opposite one of the sides 134 of auxiliary device 122. When so positioned, auxiliary device 122 takes readings of the patient's temperature and reports them to controller 22.

Controller 22 compares the temperature reading(s) taken from the finger(s) of the users left hand with the temperature reading(s) taken from the finger(s) of the users right hand. Controller 22 does not need to know which sensors correspond to the right hand and which correspond to the left hand. Instead, controller 22 looks for differences in the temperature readings. This is done because differences in temperature between the right and left sides of a person's body are a potential indicator of a stroke. The measured temperature difference 140 (FIG. 6), if any, is assigned a score by controller 22 that is used, along with the other test results, when determining whether to issue notifications at step 106 or 108 (FIG. 5).

Controller 22 of the first embodiment of auxiliary device 122 is also configured to request as part of step 102 that the user utilize electrodes 126 to enable main device 120 to take an ECG reading of the user. This request can occur before, after, or during the facial droop, arm, and speech tests of FIGS. 2A-4B, as well as before or after the temperature tests just described. When requesting an ECG reading, controller 22 displays instructions on display 30 of main device 120 requesting that the user position specific fingers on each of ECG electrodes 126 and hold them there while ECG data is collected. After the ECG data is collected, controller 22 issues an aural and/or visual indication to the user indicating that they may now remove their fingers from electrodes 126. Controller 22 is programmed to analyze the ECG to look for any signs of cardiac dysrhythmia, atrial fibrillation, or other conditions that are indicators of increased stroke risk. Controller 22 assigns a numeric score to the results of the ECG readings and uses them, along with the other test results, when determining whether to issue notifications at steps 106 or 108 (FIG. 5).

The connection between auxiliary device 122 and main device 120 can take on a variety of different forms. In one embodiment, auxiliary device 122 includes a microphone plug that plugs into microphone jack 38 of main device 120. The plug is in communication with sensors 124 and electrodes 126. In some embodiments, auxiliary device 122 includes its own controller (such as a microcontroller, or other type) that processes the outputs from sensors 124 and electrodes 126 before sending the processed results to main controller 22. In another embodiment, auxiliary device 122 includes a USB cable that plugs into USB port 36 of main device 120, thereby enabling communication of the data from sensors 124 and electrodes 126 to main controller 22.

In a second embodiment of stroke detection device 220, temperature sensors 124 are used to passively monitor for signs of a potential stroke while the user normally uses main device 120. In this embodiment, temperature sensors 124 are positioned at locations on auxiliary device 122 that a user's fingers are likely to come into contact with when grasping auxiliary device 122. Thus, as shown in FIG. 7, two temperatures sensors 124 are positioned along a first one of sides 134 and two other temperature sensors 124 are positioned along a second one of sides 134. When the user is using main device 120 to make a phone call, it is likely that at least one of his or her fingers will make contact with at least one of these sensors 124 during the phone call, thereby enabling a temperature reading of that person's fingers to be made. Such temperature readings are stored, time stamped, and used for comparison purposes when temperature readings from the opposite side of the patient's body are collected.

In at least one embodiment, controller 22 is adapted to automatically determine which hand a user is holding main device 120 with when the user is making a phone call. This automatic determination is made based upon data from the accelerometer 28 indicating which way main device 120 is tilted relative to the face of main device 120 that includes display 30, as well as the presumption that the user will hold the phone at an slant during a phone call such that the speaker (not shown) of stroke detection device 220 is aligned with the person's ear and the microphone 40 is positioned near the person's mouth. Controller stores the temperature readings along with the automatic determination of which side of the body they originated from. This allows controller 22 to compare the temperature readings to other temperature readings that were taken from the opposite side of the body.

In some embodiments, controller 22 may issue a request on display 30 for the user to identify which hand the user currently has in contact with one or more temperature sensors 124. If controller 22 does not have a recent temperature reading from the user's other side of the body, controller 22 will issue another request for the user to place his or her opposite hand in contact with one or more of temperatures sensors 124. This will give controller 22 sufficient temperature data to measure a temperature difference between the sides of the patient's body.

In an alternative embodiment, auxiliary device 122 includes a top and bottom temperature sensors 124a and 124b, which are illustrated in dashed lines in FIG. 7. In this alternative embodiment, controller 22 is programmed to take temperature readings from the user when he or she is using the keyboard of main device 120, such as during texting or at other times. Most users of cell phones will hold the cell phone with his or her right hand on one side of the phone and his or her left hand on the other side of the phone. Depending upon the orientation which the user holds the phone, sensors 124a and 124b will record temperature readings from opposite ones of the user's hands, or sensors 124 on a first side 134 and sensors 124 on the opposite side 134 of auxiliary device 122 will record temperature readings from opposite ones of the user's hands. Controller 22 will therefore receive temperature readings of the user's temperature from different sides of the body every time the user utilizes the keyboard of main device 120. This facilitates passive monitoring of temperature difference 140. When controller 22 detects temperature differences that exceed a threshold, it prompts the user to take additional tests at step 102 of method 90 (FIG. 5).

Although auxiliary device 122 is shown in FIG. 7 as having a generally flat back face 128, generally straight sides 134, and a generally straight top and bottom 130 and 132, in other embodiments, auxiliary device 122 is contoured or otherwise shaped to define recesses that the users fingers naturally fit into when gripping auxiliary device 122, thereby encouraging alignment of the users fingers with one or more temperature sensor 124 while grasping the main device 120 during a phone call, or when using device 120 for other purposes.

Figure 8:
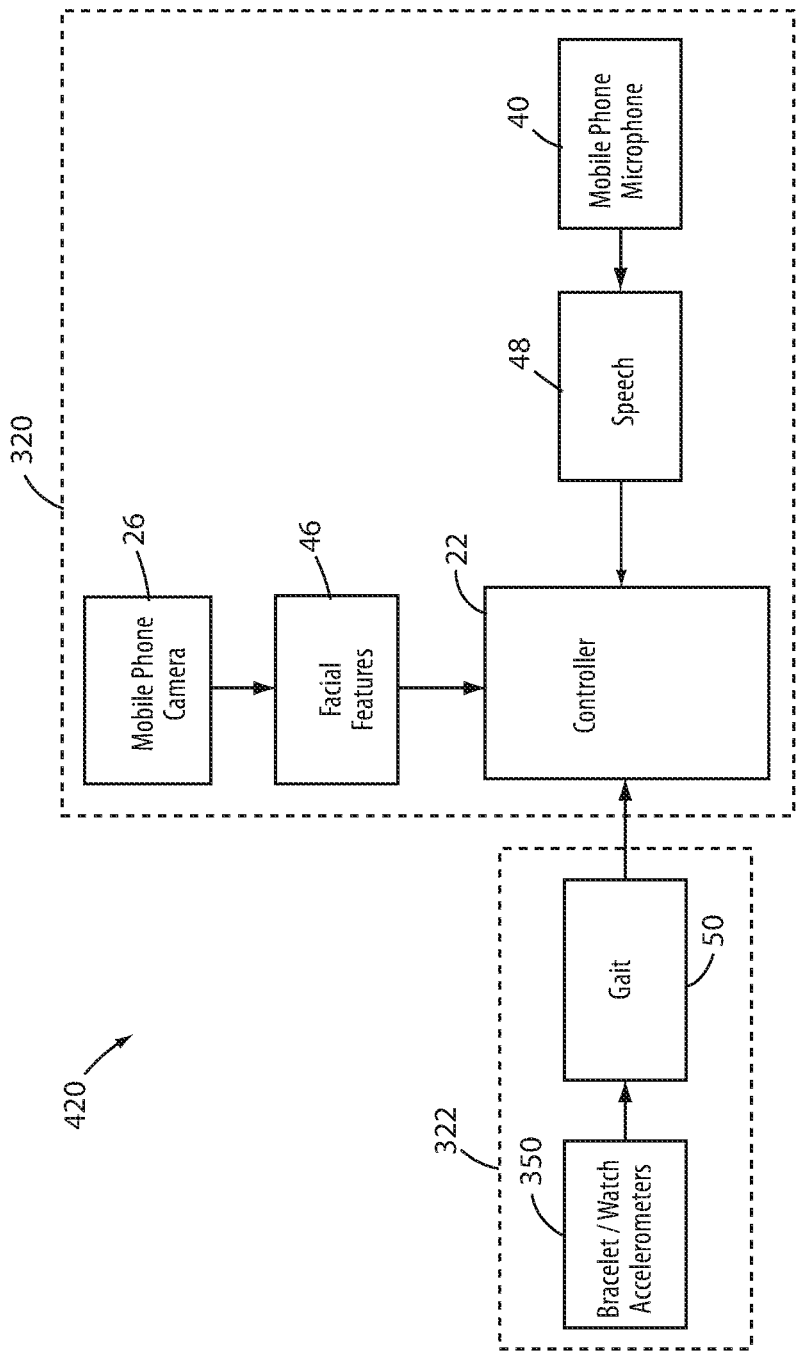
FIG. 8 is a block diagram of a third embodiment of a stroke detection device.

FIG. 8 illustrates another alternative embodiment of a stroke detection device 420 according to the present disclosure. Stroke detection device 420 includes a number of components in common with stroke detection device 20 (and 220), as well as one or more components that are not found in these stroke detection devices. Those components that are the same as, and operate in the same manner as previously described, are labeled in stroke detection device 420 with the same reference numbers as were used with stroke detection devices 20 or 220. Those components that are new are labeled with a new number, and those components that are similar, but modified in some way, bear the same reference number as found in stroke detection devices 20 or 220 but increased by two hundred.

Stroke detection device 420 of FIG. 8 is similar to stroke detection device 220 of FIG. 6 in that it includes two separate devices: a main device 320 and an auxiliary device 322. Main device 320 is physically implemented as a cell phone in FIG. 8, although it may be implemented in other physical forms in other embodiments, as will be discussed more below. Stroke detection device 420 differs from stroke detection device 220 in several manners: (1) the user characteristics sensed by main device 320 are different from those sensed by main device 120, (2) the user characteristics sensed by auxiliary device 322 are different from those sensed by auxiliary device 122, and (3) the physical form of auxiliary device 322 is different from the physical form of auxiliary device 122.

Before explaining those differences in greater detail, it is to be noted that, as with main device 120 of FIG. 6, main device 320 of FIG. 8 is not shown with all of its internal components for purposes of avoiding excessive clutter. Indeed, none of the main devices (520, 720, 920, 1120, and 1320) of FIGS. 9-13 are shown with all of their internal components. All of these main devices (320, 520, 720, 920, 1120, and 1320) do, however, contain all of the components of stroke detection device 20 of FIG. 1, in at least one of their respective embodiments (e.g. a memory 24, an accelerometer 28, a display 30, a USB port 36, a cellular transceiver 32, a microphone jack 38, and, in some embodiments, one or both of a WiFi transceiver 34 and SIM card 42). Further, although also not shown in FIGS. 8-13 for purposes of clarity, all of these main devices (320, 520, 720, 920, 1120, and 1320) are capable of communicating with one or more designated individuals 82, hospitals 84, and/or monitoring centers 86, in any of the manners previously described.

Memory 24 of main device 320 includes a stroke detection app that includes all of the features and functions of stroke detection app 44, but that has been modified to work in conjunction with auxiliary device 322. That is, as will be described in greater detail below, controller 22 is programmed to receive user gait data from auxiliary device 322, either in lieu of or in addition to, gait data gathered from accelerometers 28 included within main device 320.

Auxiliary device 322 of FIG. 8 is physically configured as a user-wearable device, such as a bracelet, watch, or other attachment to the user's body. Auxiliary device 322 communicates with main device 320 wirelessly, in one embodiment, and via a cable in another embodiment. In one of the wireless embodiments, auxiliary device 322 communicates with main device 320 via Bluetooth. In other wireless embodiments, other communication protocols are used.

Auxiliary device 322 includes one or more auxiliary accelerometers 350. Auxiliary accelerometers 350 are used in the same manner as main accelerometers 28 described previously. That is, the outputs from auxiliary accelerometers 350 are used to assess the users gait 50. In one embodiment of auxiliary device 322, this gait assessment takes place automatically and passively whenever auxiliary device 322 is being used. The results of these automatic assessments are forwarded to controller 22 and controller 22 determines whether they are indicative of a change in the user's gait or not. If so, controller 22 moves to step 102 of method 90 and requests that the user perform additional tests to better gauge the likelihood that the user has experienced a stroke. In another embodiment, the outputs from auxiliary accelerometers 350 are only used when controller 22 is engaged in test 102. In other words, in this alternative embodiment, accelerometers 350 do not trigger the taking of additional tests at step 102, but instead are part of the additional tests at step 102, and the decision to proceed to step 102 is triggered by other data received by controller 22.

In one modified embodiment of stroke detection device 420, auxiliary device 322 includes an internal processor, microcontroller, or other type of controller that is separate from the controller 22 of main device 320. In such an embodiment, the auxiliary device controller processes the outputs from the auxiliary accelerometers 350 before sending the results to controller 22. This offloads the computational load of the gait analysis from controller 22, thereby freeing it to perform other tasks.

Figure 9:
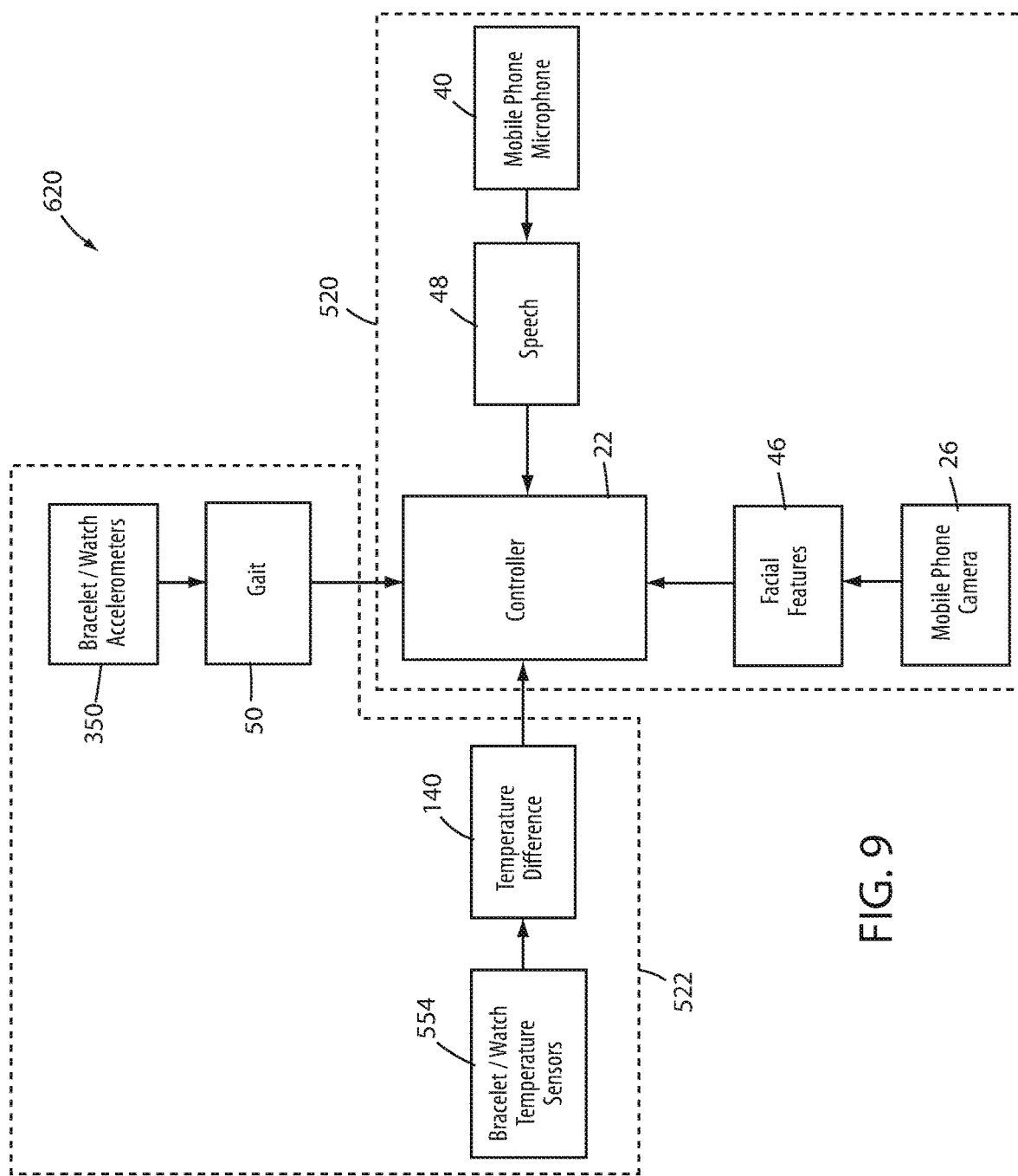
FIG. 9 is a block diagram of a fourth embodiment of a stroke detection device.

FIG. 9 illustrates another alternative embodiment of a stroke detection device 620 according to the present disclosure. Those components of stroke detection device 620 that are common to one or more of the previously described stroke detection devices (20, 220, and 420) and that operate in the same manner as previously described are labeled in stroke detection device 620 with the same reference number. Those components that are new are labeled with a new number, and those components that are similar, but modified in some way, bear the same reference number as found in the previously described stroke detection device but increased by two hundred.

Stroke detection device 620 includes a main device 520 and an auxiliary device 522. Main device 520 is physically implemented as a cell phone in FIG. 9, although it may be implemented in other physical forms in other embodiments, as will be discussed more below. Main device 520 is the same as main device 320 with the exception that the stroke detection app executed by controller 22 of main device 520 has been modified to receive temperature difference readings from an auxiliary device, which the stroke detection app of main device 320 does not do. The structure and functions of main device 520 have therefore been previously described.

Auxiliary device 522 is physically configured as a pair of two user-wearable devices. A first one of the user-wearable device is worn on the users right arm or wrist, and the second one is worn on the user's left arm or wrist. In one embodiment, both the first and second user-wearable devices are bracelets. In another embodiment, both the first and second user-wearable devices are watches. In still other embodiments, one of the user-wearable devices is a watch and the other of the user-wearable device is a bracelet.

Regardless of the specific physical form of the two wearable devices of auxiliary device 522, at least one of the wearable devices includes an accelerometer 350 (or multiple accelerometers 350) for monitoring the users gait 50. The one or more accelerometers 350 are the same as, and operate in the same manner as, accelerometer 350 of auxiliary device 322 (FIG. 8), and therefore need not be described further. In some embodiments, both of the two wearable devices of auxiliary device 522 include an accelerometer 350.

Each of the two wearable devices of auxiliary device 522 also include a temperature sensor 554 that is adapted to contact the users skin and measure the temperature of the user. By including such a temperature sensor 554 in each of the two user-wearable devices, and by the user wearing one of the user-wearable devices on his or her right arm or wrist and the other one of the user-wearable devices on his or her left arm or wrist, temperature readings from the right and left sides of the user's body are collected. A temperature difference 140 between these two temperature readings can therefore be determined and used by controller 22 in assessing the possibility of a stroke.

In one embodiment, each user-wearable device of auxiliary device 522 separately reports its temperature readings to controller 22 via its own communication connection (e.g. Bluetooth). In another embodiment, a first one of the user-wearable devices reports its temperature reading (and accelerometer readings, if accelerometer 350 is present) to a second one of the user-wearable devices, and the second user-wearable device then reports both its readings and those from the first user-wearable device to controller 22. Controller 22 utilizes the reported temperature differences 140 in any of the manners previously described with respect to stroke detection device 220 and the temperature differences 140 reported by auxiliary device 122 (FIG. 6).

Figure 14:
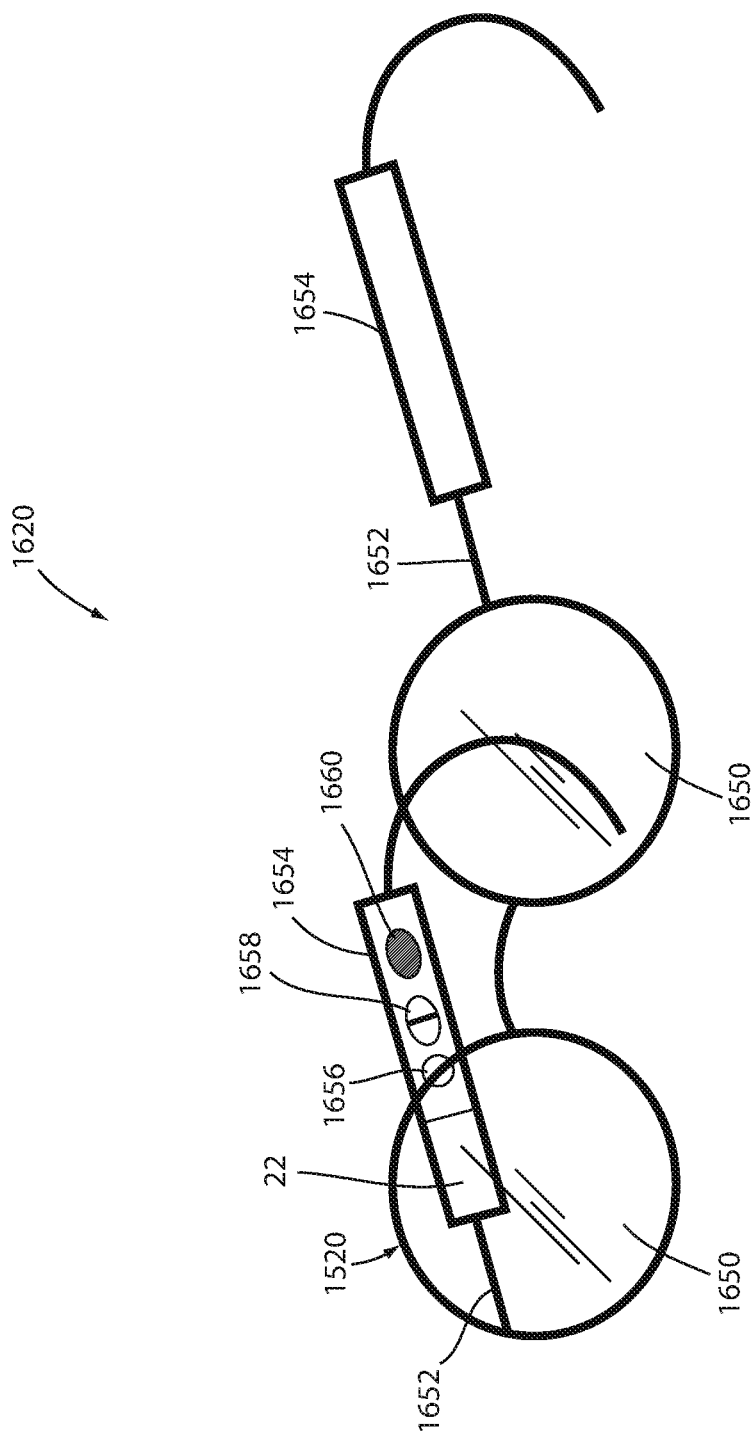
FIG. 14 is a perspective view of a ninth embodiment of a stroke detection device.

In a modified embodiment of stroke detection device 620 of FIG. 9, auxiliary device 522 is modified to comprise a single user-wearable device that is capable of measuring temperature differences between the user's right and left sides, rather than two separate user-wearable devices. In one such modified embodiment, auxiliary device 522 is a pair of eyeglasses having a temperature sensor positioned along each one of the temple tips of the eyeglasses so that the temperature from the users right temple and the users left temple can be monitored whenever the user is wearing the eyeglasses. One version of such eyeglasses are shown in FIG. 14 and described in more detail below. Accelerometer 350 may also be included in the eyeglasses. The temperature readings from the user's right and left temples and the accelerometer data (if present) are forwarded to controller 22 for use in assessing the possibility of a stroke.

Figure 10:
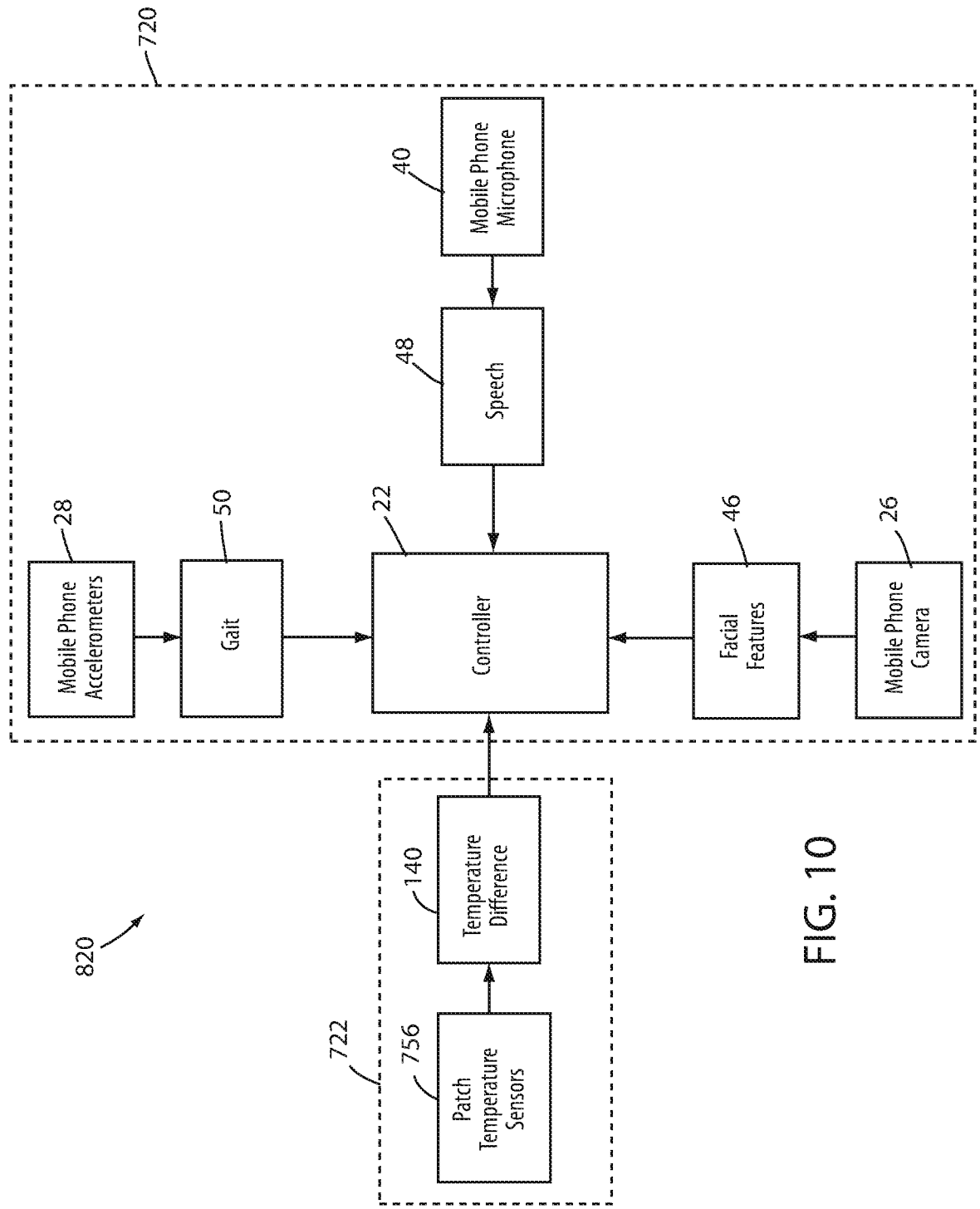
FIG. 10 is a block diagram of a fifth embodiment of a stroke detection device.

FIG. 10 illustrates another alternative embodiment of a stroke detection device 820 according to the present disclosure. Those components of stroke detection device 820 that are common to one or more of the previously described stroke detection devices (20, 220, 420, and 620) and that operate in the same manner as previously described are labeled in stroke detection device 820 with the same reference number. Those components that are new are labeled with a new number, and those components that are similar, but modified in some way, bear the same reference number as found in the previously described stroke detection device but increased by two hundred.

Stroke detection device 820 includes a main device 720 and an auxiliary device 722. Main device 720 is physically implemented as a cell phone in FIG. 10, although it may be implemented in other physical forms in other embodiments, as will be discussed more below. Main device 720 is the same as main device 120 with the exception that the stroke detection app executed by controller 22 of main device 720 does not receive ECG signals from an auxiliary device, such as main device 120 does. The structure and functions of main device 720 have therefore been previously described.

Auxiliary device 722 is physically configured as a plurality of user wearable patches that are secured to the user's skin and that include each include a patch temperature sensor 756. A first one of the patches is secured to a location on the right side of the users body and a second one of the patches is secured to a location on the left side of the users body. The patches report the temperature of the user measured at their respective locations to controller 22 which uses the temperature difference 140 (if any) in assessing the possibility of a stroke, including whether to institute additional testing (e.g. step 102 of FIG. 5).

In one embodiment of auxiliary device 722, each patch includes its own wireless transceiver and communicates its temperature readings wirelessly to main device 720. In another embodiment, each patch is coupled by a wire to a common transceiver that communicates the temperature readings from each sensor 756 to main device 720. In still another embodiment, each patch is equipped with a near-field transponder that responds to near field interrogation signals with both an ID code and the temperature readings from its temperature sensor 756. In this embodiment, main device 720 is equipped with a near field transceiver that is capable of emitting a near field interrogation signal to the patches when main device 720 is moved within close physical proximity to the patches (0-20 centimeters, for example, although other ranges are possible). Such near field transceivers are common in conventional cell phones. Accordingly, when main device 720 is physically implemented as such a cell phone, it does not need any physical modification to be able to interrogate such patches using near field communication.

Figure 11:
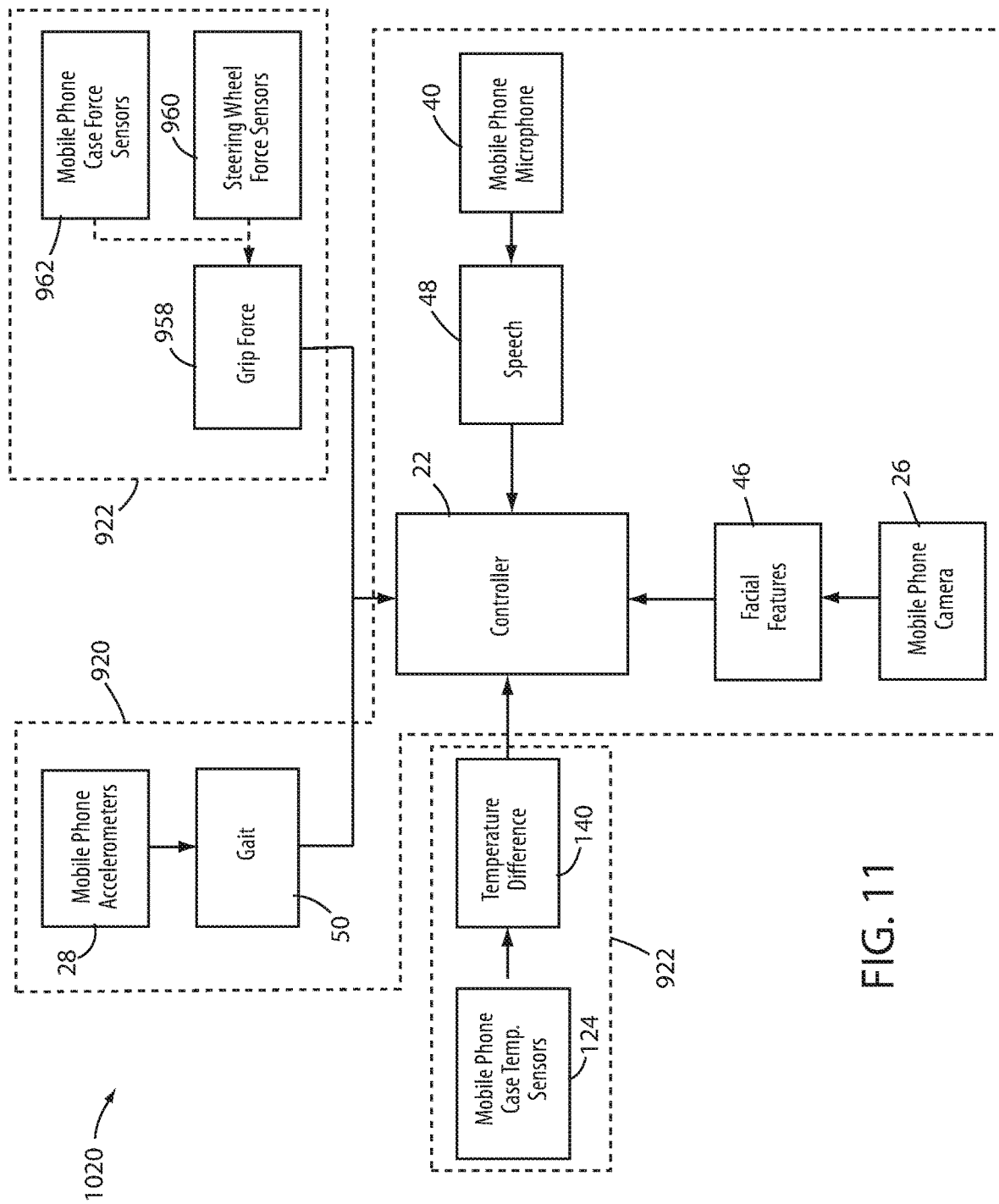
FIG. 11 is a block diagram of a sixth embodiment of a stroke detection device.

FIG. 11 illustrates another alternative embodiment of a stroke detection device 1020 according to the present disclosure. Those components of stroke detection device 1020 that are common to one or more of the previously described stroke detection devices (20, 220, 420, 620, and 820) and that operate in the same manner as previously described are labeled in stroke detection device 1020 with the same reference number. Those components that are new are labeled with a new number, and those components that are similar, but modified in some way, bear the same reference number as found in the previously described stroke detection device but increased by two hundred.

Stroke detection device 1020 includes a main device 920 and one or more auxiliary devices 922. Main device 920 is physically implemented as a cell phone in FIG. 11, although it may be implemented in other physical forms in other embodiments, as will be discussed more below. Main device 920 is the same as main device 120 with the exception that the stroke detection app executed by controller 22 of main device 920 also receives grip force and temperature measurements from one or more auxiliary devices 922, which main device 120 does not. Main device 920's use of these grip force measurements are discussed in greater detail below.

Auxiliary device 922 is broken up into two separate boxes in FIG. 11. It will be understood that this does not necessarily represent the physical configuration of auxiliary device 922. That is, in one embodiment, auxiliary device 922 is a single physical unit, such as a mobile phone case. In another embodiment, auxiliary device 922 is a pair of physically separate units, such as a cell phone case and an automobile steering wheel.

Regardless of whether or not auxiliary device 922 is broken up into two separate physical components or not, it is adapted to measure the temperature difference 140 between the right and left sides of the users body. Temperature difference 140 is reported to controller 22 in any of the ways described above and used for any of the purposes already described. Temperature difference 140 is measured by one or more temperature sensors 124 integrated into a mobile phone case.

Stroke detection device 1020 also includes one or more sensors for monitoring a users grip force 958. Grip force 958 is monitored either by one or more force sensors 960 built into an automobile steering wheel, or by one or more force sensors 962 built into the mobile phone case. Regardless of where the force sensors are physically located, the stroke detection app executed by controller 22 of stroke detection device 1020 requests that the user input maximum baseline grip force readings when the stroke detection app is initially set up. These are input by having the user squeeze the force sensors 960 or 962 as hard as he or she can while the outputs from the sensors are recorded by controller 22. A separate maximum baseline grip force reading is obtained for the user's right and left hands.

Once the maximum baseline grip force readings are stored and retained, controller 22 includes a grip force test in step 102 of method 90. That is, in at least one embodiment, subsequent measurements of the user's maximum grip force 958 are taken whenever controller 22 executes step 102. Such maximum grip force measurements may be taken before, after, or in between any one of the facial droop, arm, speech, temperature difference, and/or gait measurements previously discussed (some or all of which may be included as part of test 102, depending upon the particular embodiment of the stroke detection device).

In another embodiment, grip force sensors 960 and/or 962 are used to take additional normal baseline grip force readings where force sensors 960 and/or 962 measure the users normal amount of force (rather than maximum force) when gripping the steering wheel or cell phone case. Once these normal baseline readings are taken, the grip force sensors 960 or 962 are automatically monitored by controller 22 during the usage of main device 920 and compared to the normal baseline grip forces. If there is a significant change in the measured grip force 958 relative to the normal baseline grip force, then controller 22 executes additional steps at step 102 of method 90. The measurement of the users normal grip force 958 may therefore be used as a trigger for executing step 102 in some embodiments.

In some embodiments, the users normal grip force is used as a trigger for executing step 102, and the users maximum grip force is measured as part of one of the tests executed during step 102. That is, a change in the users normal grip force for holding the cell phone case or steering wheel triggers step 102. During step 102, controller 22 asks the user to squeeze the force sensors 960 or 962 as hard as he or she can with his or her right hand, and then with his or her left hand. The results are then compared to the baseline maximum force readings for the user's right and left hands and assigned a numerical score. Depending upon the score, as well as the scores from the other tests executed at step 102, controller 22 subsequently determines whether to proceed to notification steps 106 or 108 in method 90.

When auxiliary device 922 includes force sensors 960 integrated into a steering wheel of an automobile, the force sensors 960 communicate their readings to controller 22 in any of the manners discussed above (such as, but not limited to, Bluetooth). Further, such automobile force sensors 960 are positioned around substantially the entire perimeter of the steering wheel such that no matter where the user grips the steering wheel, force measurements can be obtained. In one such embodiment, the force sensors are positioned inside the steering wheel such that they are not visible to the user. In another embodiment, they are positioned outside of the steering wheel and visible to the user.

In still another embodiment, controller 22 analyzes the outputs from force sensors 960 to determine whether there is any significant change between the normal forces exerted by the users right and left hands while gripping the steering wheel. That is, rather than, or in addition to, looking at the magnitude of the forces detected by sensors 960, controller 22 alternatively, or additionally, looks at the difference between the force sensors to determine if there is a change between the user's right and left hand gripping force that exceeds a corresponding baseline reading by more than a threshold. If so, controller 22 proceeds to step 102 of method 90.

Figure 12:
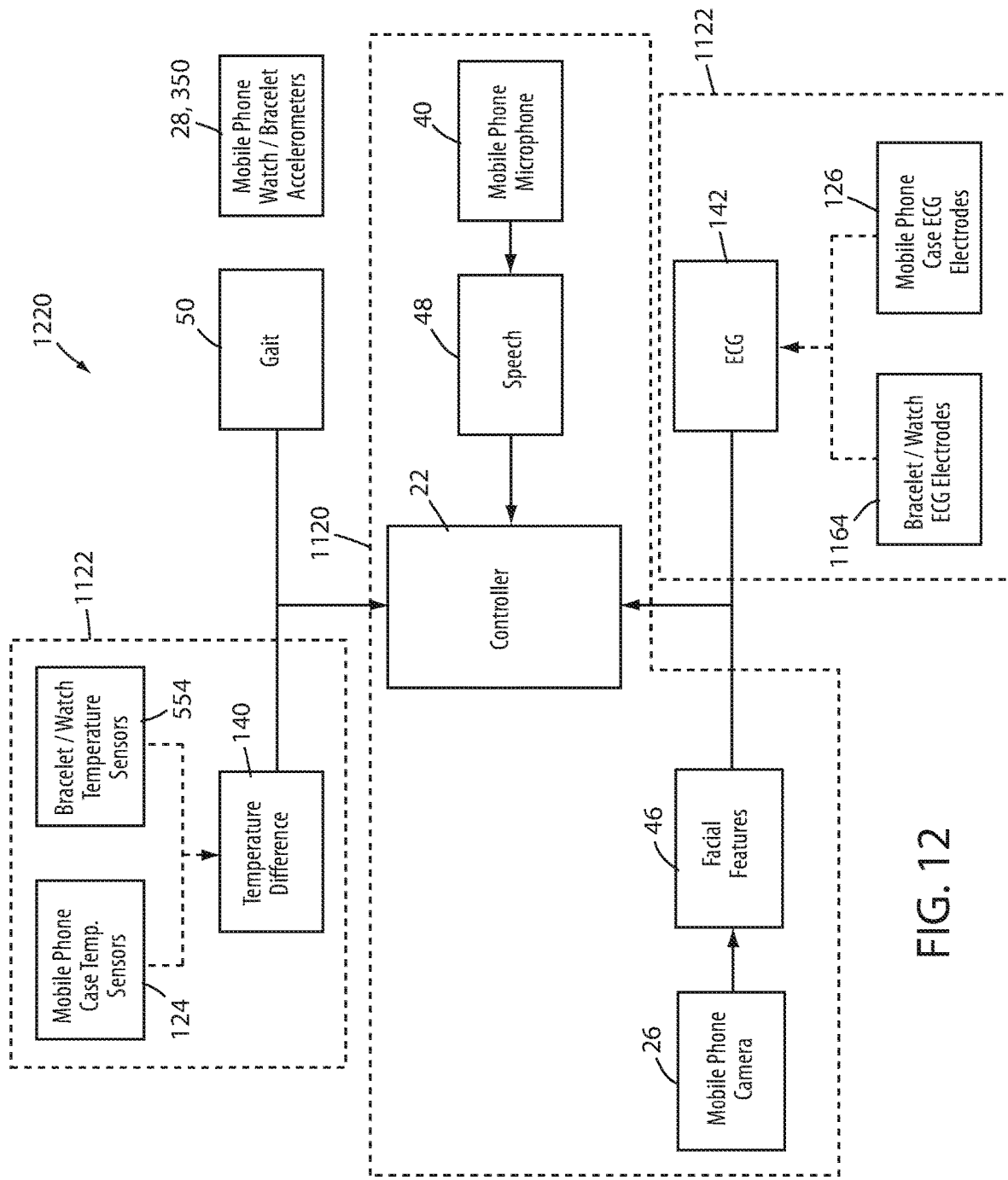
FIG. 12 is a block diagram of a seventh embodiment of a stroke detection device.

FIG. 12 illustrates another alternative embodiment of a stroke detection device 1220 according to the present disclosure. Those components of stroke detection device 1220 that are common to one or more of the previously described stroke detection devices (20, 220, 420, 620, 820, and 1020) and that operate in the same manner as previously described are labeled in stroke detection device 1220 with the same reference number. Those components that are new are labeled with a new number, and those components that are similar, but modified in some way, bear the same reference number as found in the previously described stroke detection device but increased by two hundred.

Stroke detection device 1220 includes a main device 1120 and one or more auxiliary devices 1122. Main device 1120 is physically implemented as a cell phone in FIG. 12, although it may be implemented in other physical forms in other embodiments, as will be discussed more below. Main device 1120 is the same as main device 520 with the exception that the stroke detection app executed by controller 22 of main device 1120 also receives ECG measurements from an auxiliary device, which main device 520 does not.

Auxiliary device 1122 is broken up into two separate boxes in FIG. 12. It will be understood that this does not necessarily represent the physical configuration of auxiliary device 1122. That is, in one embodiment, auxiliary device 1122 is a single physical unit, such as a mobile phone case. In another embodiment, auxiliary device 1122 is a pair of physically separate units, such as a pair of bracelets, a pair of watches, one watch and one bracelet, one mobile phone case and one bracelet, or one mobile phone case and one watch. In still another embodiment, auxiliary device 1122 includes three physically separate components, such as a mobile phone case, a watch, and a bracelet.

FIG. 12 also illustrates an accelerometer 28 or 350 for monitoring the user's gait 50. Accelerometer 28, 350 is not shown as part of either main device 1120 or auxiliary device 1122. This has been done because this accelerometer may be part of either, or it may be part of neither. That is, in some embodiments, accelerometer 28, 350 is incorporated into main device 1120. In other embodiments, it is incorporated into auxiliary device 1122. In still other embodiments, it is incorporated into a second auxiliary device that is physically separate from auxiliary device 1122. Regardless of the physical form of accelerometer 28 or 350, it is configured to monitor the users gait and report gait data to controller 22 in any of the manners previously described.

Regardless of whether or not auxiliary device 1122 is broken up into separate physical components or not, it is adapted to measure the temperature difference 140 between the right and left sides of the users body. Temperature difference 140 is reported to controller 22 in any of the ways described above and used for any of the purposes already described. Temperature difference 140 is measured by one or more temperature sensors 124 integrated into a mobile phone case, or by multiple temperature sensors 554 integrated into a pair of watches, a pair of bracelets, or a watch/bracelet pair (or a pair of eyeglasses).

Stroke detection device 1220 also includes electrodes for taking ECG readings 142 from the user. In one embodiment, auxiliary device 1122 is a mobile phone case that includes ECG electrodes 126, as described previously with respect to stroke detection device 220. In another embodiment, auxiliary device 1122 is a pair of bracelets, a pair of watches, or a bracelet and watch pair wherein each item in the pair includes at least one ECG electrode 1164. The outputs from the ECG electrodes 1164 are forwarded to controller 22 for analysis and use in any of the manners previously described.

Figure 13:
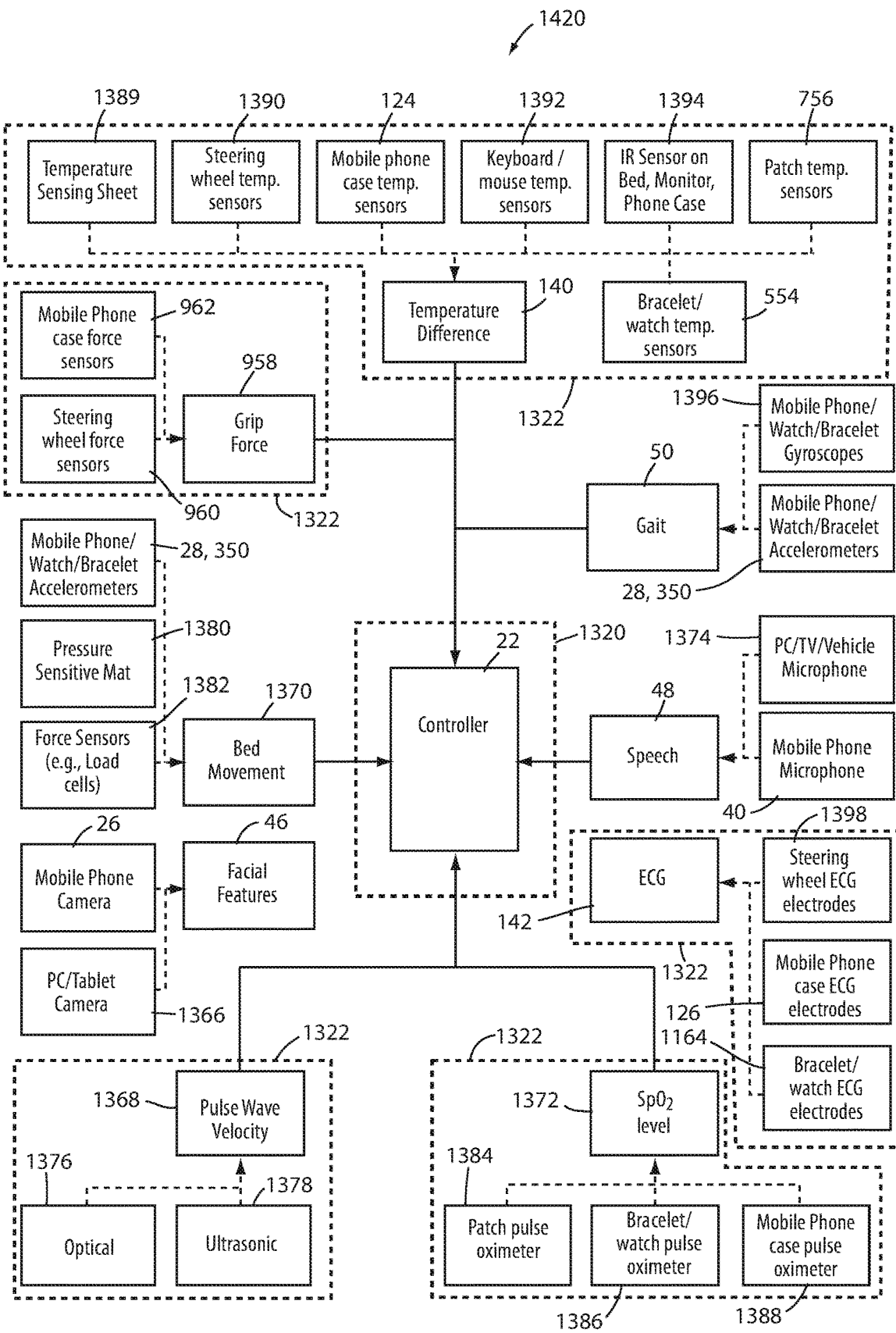
FIG. 13 is a block diagram of an eighth embodiment of a stroke detection device.

FIG. 13 illustrates another alternative embodiment of a stroke detection device 1420 according to the present disclosure. Those components of stroke detection device 1420 that are common to one or more of the previously described stroke detection devices (20, 220, 420, 620, 820, 1020, and 1220) and that operate in the same manner as previously described are labeled in stroke detection device 1420 with the same reference number. Those components that are new are labeled with a new number, and those components that are similar, but modified in some way, bear the same reference number as found in the previously described stroke detection device but increased by two hundred.

Stroke detection device 1420 includes a main device 1320 and one or more auxiliary devices 1322. Main device 1320 is physically implemented as a cell phone in FIG. 13, although it may be implemented in other physical forms in other embodiments, as will be discussed more below. Main device 1320 is shown in FIG. 13 as only including controller 22. This has been done for clarity purposes and to illustrate that the precise composition of main device 1320 can be varied. For example, in one embodiment none of the user characteristics that are tested or monitored (i.e. facial features 46, speech 48, gait 50, temperature differences 140, ECG 142, grip force 958, pulse wave velocity 1368, bed movement 1370, and oxygen saturation levels (SpO$_2$) 1372) by stroke detection device 1420 are measured by sensors contained within main device 1320. In such an embodiment, all of the user characteristics that are tested or monitored are sensed by sensors that are part of one or more auxiliary devices 1322. In still other embodiments, one or more of these user characteristics are sensed by sensors built into main device 1320 while the remaining characteristics are sensed by sensors integrated into one or more of the auxiliary devices 1322.

Also, despite main device 1320 being illustrated in FIG. 13 as having no components besides controller 22, it will be understood that main device 1320 does include microphone 40, camera 26, and accelerometers 28, even though these components are not shown inside of the dashed lines corresponding to main device 1320. Finally, as noted earlier, main device 1320 includes all of the components of stroke detection device 20 that are not shown in FIG. 13, in at least one embodiment (i.e. cellular transceiver 32, microphone jack 38, display 30, USB port 36, and in some embodiments one or both of WiFi transceiver 34 and SIM card 42).

Auxiliary device 1322 is broken up into five separate boxes in FIG. 13. It will be understood that this does not necessarily represent the physical configuration of auxiliary device 1322. That is, auxiliary device 1322 may include anywhere from one to five or more physically separate components. As can be seen in FIG. 13, the particular components of auxiliary device 1322 vary and include, but are not limited to, watches, bracelets mobile phone cases, steering wheels, keyboards, IR sensors, patches, pressure sensing mats, and others.

FIG. 13 also illustrates a number of components that are not shown as part of either main device 1320 or auxiliary device 1322. This has been done because these components may be part of either one of these devices 1320, 1322, or they may be separate from device 1320 and one or more of the other auxiliary devices 1322. Thus, for example, the user's facial features may be monitored in one embodiment by a camera 26 incorporated into the microphone 40 that is part of main device 1320, or they may be monitored by a camera 1366 that is part of a laptop computer, a tablet computer, or a desktop computer. Camera 1366, in turn, may be physically separate from one or more other auxiliary devices 1322, such as, for example, an automobile steering wheel or a bracelet.

Stroke detection device 1420 differs from the previously described stroke detection devices in that it is capable of monitoring and/or testing three additional characteristics of the user: pulse wave velocity 1368, bed movement 1370, and oxygen saturation levels (SpO$_2$) 1372. Stroke detection device 1420 also differs from the previously described stroke detection devices in that it includes a number of additional physical forms in which sensors may be integrated for monitoring or testing the previously described user characteristics. For example, the user's speech 48 may be monitored either by microphone 40 of main device 1320, or by an auxiliary microphone 1374. As shown in FIG. 13, auxiliary microphone 1374 is integrated into any one of a desktop computer, a television, and a vehicle. Auxiliary microphone 1374 is used in the same manners as previously described for microphone 1374.

Before turning to a detailed description of stroke detection device 1420, it should also be noted that the illustration of multiple different items in FIG. 13 (and FIGS. 11 and 12) for detecting a particular characteristic of the user is not intended to imply that all of these multiple components are present in the stroke detection device 1420. Instead, these multiple components are included in the drawing to illustrate the different options that may be used for different embodiments of the stroke detection device. This optional nature is indicated by the dashed lines that connect these multiple components to the corresponding user characteristic. Thus, for example, in FIG. 13, the inclusion of both mobile phone microphone 40 and auxiliary microphone 1374 for sensing the user's speech 48 is not intended to imply that both of these microphones need be present in stroke detection device 1420. Instead, it is intended to illustrate that stroke detection device 1420 includes at least one of these two (and in some embodiments can include both).

Turning now to the first of the three additional user characteristics that stroke detection device 1420 is capable of monitoring and/or testing, main device 1320 is in communication with an auxiliary device 1322 that is adapted to detect a user's pulse wave velocity 1368. The detection of the users pulse wave velocity 1368 is carried out either using one or more optical sensors 1376 or one or more ultrasonic sensors 1378. From the detected pulse wave velocity, either auxiliary device 1322 or controller 22 calculates the users blood pressure. Abrupt changes in the users blood pressure may be indicative of a stroke. Auxiliary device 1322 or controller 22 therefore monitors the user's blood pressure for such changes. If such a change is detected, controller 22 moves to step 102 of method 90 and institutes one or more additional tests. In another embodiment, controller 22 does not monitor the users pulse wave velocity or blood pressure until another triggering event prompts controller 22 to step 102 of method 90. Pulse wave velocity readings can therefore either be passively monitored and used to trigger controller 22 to move to step 102, or they may be part of the plurality of tests implemented by controller 22 at step 102.

In at least one embodiment, the user's pulse wave velocity 1368 is measured using one of the pulse wave velocity measuring devices disclosed in commonly assigned U.S. patent application Ser. No. 62/072,669 filed Oct. 30, 2014, by inventors Sean Hadley et al. and entitled SYSTEMS AND METHODS FOR DETECTING PULSE WAVE VELOCITY, the complete disclosure of which is hereby incorporated herein by reference. Other types of pulse wave velocity sensors can also be used.

With respect to the second of the three additional user characteristics that stroke detection device 1420 is capable of monitoring and/or testing, main device 1320 is in communication with an auxiliary device 1322 that is adapted to detect a user's bed movement 1370. Bed movement 1370 refers to the movement of the user while he or she is lying down on a bed, or other support apparatus, and sleeping. A potential indicator of a stroke is the lack of movement of a sleeping person for a longer than normal amount of time for that individual. Controller 22 therefore monitors the user's bed movement 1370 for signs of a potential stroke.

The monitoring of the user's bed movement 1370 is carried out with respect to one or more baseline movement readings that are taken when the user is asleep and at the time stroke detection device 1420 is initially set up. These baseline movement readings are stored within memory 24 of main device 1320 and used for comparison purposes with subsequent bed movement readings. If controller 22 detects that the user has not moved for a greater than normal time period, or that the user has moved less than is normal for that user, controller 22 is adapted to issue an audio and/or visual alert that, in at least one embodiment, is intended to awaken the user. Controller 22 then instructs the user to take one or more of the previously described tests at step 102 to determine if the user should seek prompt medical attention or not.

FIG. 13 illustrates three different physical items that may be used to monitor the user's bed movement 1370: accelerometers 28 or 350, a pressure sensitive mat 1380, and a plurality of load cells 1382 integrated into a person support apparatus (e.g. a bed, a stretcher, a sofa, a recliner, or the like). When using any of these items to measure bed movement 1370, controller 22 first determines that the user is asleep based upon one or more items of information. These include the time of day (as determined by a clock inside of main device 1320), an input on display 30 of main device 1320 that allows the user to indicate to controller 22 that he or she is going to sleep, vital sign information that comes from one or more of the other sensors that communicate data to controller 22, and/or other information that is forwarded to controller 22.

Pressure sensitive mat 1380 is a mat that is placed on top of the mattress, or other surface, that the user sleeps on. The pressure sensitive mat includes an array of pressure sensors that sense the position and orientation of the users body by detecting the pressure exerted by the patient's body pressing against the mat 1380. In some embodiments, the pressure sensitive mat 1380 is constructed in any of the manners disclosed in commonly assigned U.S. patent publication 2014-0039351 filed Oct. 14, 2013 by inventors Joshua Mix et al. and entitled SENSING SYSTEM FOR PATIENT SUPPORTS, or in commonly assigned U.S. Pat. Nos. 8,533,879, 8,161,826, or 8,966,997, all of which are issued to Taylor and which are entitled, respectively, ADAPTIVE CUSHION METHOD AND APPARATUS FOR MINIMIZING FORCE CONCENTRATIONS ON A HUMAN BODY, ELASTICALLY STRETCHABLE FABRIC FORCE SENSOR ARRAYS AND METHODS OF MAKING, and PRESSURE SENSING MAT, the complete disclosures of which are all hereby incorporated herein by reference. In other embodiments, the array of pressure sensors is integrated into the mattress itself, rather than being a physically separate covert that is placed on top of the mattress.

Load cells 1382 that are incorporated into a person support apparatus are also, or alternatively, used to monitor the user's bed movement 1370. One manner in which load cells 1382 can be used to monitor a users movement while sleeping is disclosed in commonly assigned U.S. patent application Ser. No. 62/065,242 filed Oct. 17, 2014 by inventors Marko Kostic et al. and entitled PERSON SUPPORT APPARATUSES WITH MOTION MONITORING, the complete disclosure of which is hereby incorporated herein by reference.

With respect to the third of the three additional user characteristics that stroke detection device 1420 is capable of monitoring and/or testing, main device 1320 is also in communication with an auxiliary device 1322 that is adapted to measure the $SpO_2$ levels 1372 of the user. Specifically, the auxiliary device 1322 includes a pulse oximeter integrated therein. As shown in FIG. 13, the device is a patch pulse oximeter 1384, a bracelet/watch pulse oximeter 1386, a mobile phone case pulse oximeter 1388, and/or a combination of two or more of these. The outputs of the pulse oximeters 1384, 1386, and/or 1388 are fed to controller 22 which analyzes them and looks for drops in $SpO_2$ levels 1372 that are greater than a threshold magnitude. Such drops may be indicative of a stroke. Accordingly, controller 22 alerts the user if such a drop is detected and proceeds to request that the user take additional tests at step 102.

In an alternative embodiment, $SpO_2$ levels 1372 are only measured as part of a test implemented during step 102, rather than passively monitored at times when controller 22 is not executing step 102. Regardless of whether or not the $SpO_2$ levels 1372 are monitored only during step 102, or are monitored outside of step 102, baseline $SpO_2$ levels 1372 are taken, stored, and used for comparison purposes in at least one embodiment of stroke detection device 1420.

Turning now to the physical forms of the sensors illustrated in FIG. 13 that have not previously been described, stroke detection device 1420 includes four additional options for measuring temperature difference 140. A first one of these additional options is a temperature sensing sheet 1389 that is adapted to be laid on top of a mattress, cushion, seat, or other object on which the user may sit or lie down. Temperature sensing sheet 1389 includes an array of temperature sensors that measure the temperature of the users body in those areas of the users body in which it is in contact. Individual ones of the temperature sensors in the temperature sensor array are assigned to a specific side of the users body. Thus, for example, if sensing sheet 1389 is placed on top of, or integrated into, a seat cushion, the individual temperature sensors on the right side of the cushion will report temperature readings corresponding to the users right side, while the individual temperature sensors on the left side of the cushion will report temperature readings corresponding to the user's left side. Controller 22 determines temperature difference 140 by looking at the temperature readings from the sheet 1389 that are taken from one side of the users body and the those temperature readings from sheet 1389 that are taken from the other side of the users body. Temperature difference 140 is used by controller 22 to determine whether to proceed to step 102 of method 90, or if controller 22 is already executing step 102, whether to proceed to steps 106 or 108.

The second additional option for measuring temperature difference 140 is a plurality of steering wheel temperature sensors 1390 that are integrated into a steering wheel of an automobile. Steering wheel temperature sensors 1390 are positioned around all or a majority of the perimeter of the steering wheel so that both of the users hands will be in contact with one or more temperature sensors 1390 while the person is driving. Controller 22 compares the temperature readings that are taken from each hand and determines the magnitude of temperature difference 140. Controller 22 utilizes temperature difference 140 in determining whether to move to step 102 or, if temperature difference 140 is being measured as part of a test administered during step 102, whether to proceed to step 106 or 108 of method 90 (FIG. 5).

Another additional option for measuring temperature difference 140 that is included in stroke detection device 1420 and that has not been previously described is a plurality of temperature sensors 1392 that are integrated into a physical keyboard. Keyboard temperature sensors 1392 are positioned at the top ends of a plurality of keys in the keyboard. A sufficient number of keyboard temperature sensors 1392 are included so that temperature readings from both the user's right fingers and left fingers can be obtained. As the user of the keyboard types, temperature readings from the sensors 1392 are taken and those from sensors 1392 that correspond to the user's right hand are compared against those taken from sensors 1392 that correspond to the users left hand. Both the right hand and left hand temperature readings may be averaged, or otherwise processed, before being compared. The comparison yields temperature difference 140 and controller 22 reacts to the magnitude of temperature difference 140 in the manners previously described.

The fourth additional option for measuring temperature difference 140 that is included in stroke detection device 1420 and that has not been previously described is one or more thermographic infrared (IR) sensors 1394 that are positioned at one or more locations where they are capable of detecting thermal images of the user. IR sensors 1394 capture thermal images of the user from which temperature difference 140 is computed. That is, controller 22 analyzes the thermal images from IR sensors 1394 and compares the temperature of one or more locations on first side of the user's body with the temperature of corresponding locations on the second side of the users body. This comparison yields temperature difference 140.

In some embodiments, IR sensors 1394 are positioned on a bed, recliner, or other person support apparatus that supports the user while he or she sits or lies down. In one such embodiment, IR sensors 1394 operate in any one or more of the manners disclosed in commonly assigned U.S. patent application Ser. No. 14/692,871 filed Apr. 22, 2015 by inventors Marko N. Kostic et al. and entitled PERSON SUPPORT APPARATUS WITH POSITION MONITORING, the complete disclosure of which is hereby incorporated herein by reference. In other embodiments, IR sensors 1394 are positioned on a computer monitor or screen such that the IR sensors 1394 are capable of capturing thermal images of the user while he or she uses a computer. In still other embodiments, IR sensors 1394 are incorporated into a mobile phone case such that they are capable of capturing thermal images of the user while he or she uses their mobile phone.

FIG. 13 also shows an additional sensor option for measuring the users gait 50 that has not previously been described. Specifically, stroke detection device 1420 includes the additional option of using one or more gyroscopes 1396 for monitoring the user's gait 50. Gyroscopes 1396 may be incorporated into one or more different items, such as a mobile phone case, a watch, a bracelet, or other items. Gyroscopes 1396 report angular changes along three perpendicular axes as the user walks to controller 22, which processes these and compares one or more of their characteristics to one or more baseline gait characteristics.

Finally, the last additional sensor option disclosed in FIG. 13 that has not been previously described is a plurality of ECG electrodes 1398 that are integrated into a steering wheel. ECG electrodes 1398 are positioned around all or a portion of the perimeter of the steering wheel such that the users fingers will make contact with the ECG electrodes while he or she is driving the automobile. The outputs from the ECG electrodes 1398 are forwarded to controller 22, which processes them in the same way it processes the outputs from the other ECG electrodes previously described.

It will be understood that, with respect to the stroke detection device 1420 of FIG. 13, as well as those stroke detection devices that operate in conjunction with more than one auxiliary device, the particular auxiliary device that the main device communicates with may change throughout the day. Thus, as but one example referencing stroke detection device 1420 of FIG. 13, main device 1320 may communicate with steering wheel temperature sensors 1390 and steering wheel ECG electrodes 1398 while the user is driving, and then switch to communicating with other auxiliary devices when the user stops driving, such as an IR sensor 1394 coupled the user's desktop computer and a microphone 1374 of the user's desktop computer. Thus, the specific auxiliary devices, as well as the number of auxiliary devices, that the main device is in communication with at any given time can vary, particularly as the user goes about performing different activities during his or her day. Still further, the particular user characteristics that are monitored may also vary throughout the day, depending upon what auxiliary devices are currently communicating with main device. For example, the users grip force 958 may be monitored at one point while the user is driving via steering wheel force sensors 960, and then later, when the user is not driving, the users grip force may not be monitored until the user returns to driving or uses another auxiliary device that includes grip force sensors (e.g. mobile phone case force sensors 962).

Although not illustrated in any of the stroke detection devices disclosed herein, any one of the above-described stroke detection devices may be modified to include an auxiliary device that is adapted to monitor the amount of force exerted by the user when he or she is using a physical keyboard. In such an embodiment, the auxiliary device is a keyboard that includes a plurality of force sensors that detect the amount of force the user is exerting when typing on the keyboard. An average or aggregate of these forces are compared to baseline force readings that were previously taken and recorded during the setup of the stroke detection device. In at least one embodiment, the force sensors are individually identified so that that their outputs can be assigned as corresponding to the users right or left hand. In other words, as one example, the force sensors integrated into the keys for the letters "J", "K", and "L" of a standard QWERTY keyboard are assumed to output force readings that were generated by the users right hand, while the keys for the letters "A", "S", and "D" are assumed to output force readings that were generated by the users left hand. Additional force sensors beyond these six force sensors, of course, may be included and assigned to the users right or left hand based upon their position on the keyboard. In some embodiment, baseline force readings are taken and averaged for individual fingers of the user and compared with subsequent force reading taken for those individual fingers.

If controller 22 determines that a change in force exerted by the user while typing has occurred, it alerts the user and proceeds to step 102 of method 90. The change that triggers step 102 may take on different forms, and one or more of these different forms may be included in a particular embodiment. One type of change that controller 22 looks for is a change in the force exerted by a specific one of the user's hands as compared to the baseline readings for that particular hand. When looking for this type of change, controller 22 also looks for a similar type of change in the users other hand (i.e. a change in the force exerted by the other one of the users hands as compared that to the baseline reading for that other hand). Another type of change that controller 22 may look for is a change in the difference between the average force exerted by the users right and left hands when compared to a baseline difference between the average force exerted by the users right and left hands. Still another type of change that controller 22 may look for is a change in the average force exerted by individual fingers of the user when compared to corresponding baseline measurements of the average force exerted by those individual fingers.

Any of the main devices or auxiliary devices described herein can also be further modified to include a heart rate sensor that communicates with controller 22. Such a heart rate sensor is easily incorporated into a watch, a bracelet, the cell phone case, a patch, or other items. When so incorporated, controller 22 monitors the outputs from the heart rate sensor and looks for sudden increases in the users heart rate. In some embodiments, such a sudden change is sufficient to trigger controller 22 to step 102. In other cases, such a sudden change is factored into data from one or more of the other sensors before controller 22 proceeds to step 102.

It will be understood by those skilled in the art that in any of the stroke detection devices described above that include a main device and one or more auxiliary devices, the auxiliary device may include its own separate controller for analyzing, or partially analyzing, the characteristics of the user that are sensed by that particular auxiliary device. When so included, the analyzed, or partially analyzed, results are forwarded to controller 22, thereby reducing the computational load of controller 22.

It will also be understood by those skilled in the art that the various different embodiments shown in the accompanying drawings are not an exhaustive listing of the manifold embodiments contemplated by the present disclosure. That is, in addition to the specific selection of user characteristics and sensors shown in each of FIGS. 1, 6, and 8-13, the various stroke detection devices can be additionally modified to monitor a greater or less number of user characteristics and/or to include one or more different sensors than what has been illustrated for monitoring those user characteristics.

Although the stroke detection devices described above have all been illustrated as being implemented as a cell phone, or having the main device implemented as a cell phone, it will be understood that other embodiments of the stroke detection device can be implemented on other types of computing devices, such as tablet computers, laptop computers, and/or desktop computers. In still other embodiments, the stroke detection device (or its main device) may be implemented as a dedicated device that performs no other functions (i.e. not incorporated into a cell phone or computer that is used for other functions besides stroke detection).

FIG. 14 illustrates another alternative embodiment of a stroke detection device 1620 according to the present disclosure. Those components of stroke detection device 1620 that are common to one or more of the previously described stroke detection devices (20, 220, 420, 620, 820, 1020, 1220, and 1420) and that operate in the same manner as previously described are labeled in stroke detection device 1620 with the same reference number. Those components that are new are labeled with a new number, and those components that are similar, but modified in some way, bear the same reference number as found in the previously described stroke detection device but increased by two hundred.

Stroke detection device 1620 differs from the previously described stroke detection devices in that it does not include two separate devices, such as a main device (e.g. 1320) and one or more auxiliary devices (e.g. auxiliary devices 1322). Instead, it includes only a single main device 1520 that is physically implemented as a pair of eyeglasses. Eyeglasses 1520 are intended to be worn by a person who is at potential risk for a stroke. Eyeglasses 1520 include a pair of lenses 1650 and a pair of temple frame members 1652. Attached to each of the temple frame members 1652 is a sensor array 1654. Each sensor array 1654 includes a temperature sensor 1656, a multi-wavelength light source 1658, and a photodetector 1660. At least one of the sensors arrays 1654 (and in some embodiments both of the sensor arrays 1654), include a controller 22 and associated electronics (e.g. a memory, communication circuitry, and a battery) for carrying out the functions described herein.

Each temperature sensor 1656 is adapted to measure a temperature of the wearer at an adjacent location (e.g. the wearers temple). Controller 22 compares the readings received from each temperature sensor 1656 and compares them to each other. If a difference exists between the two temperature readings that exceeds a predetermined size threshold and/or that persists for more than a predetermined time threshold, controller 22 concludes that the wearer may have experienced, or may be experiencing, a stroke. In such cases, controller 22 issues an alert. The alert may take on a variety of different forms. In one embodiment, the alert is an audio alert issued from a speaker, buzzer, or other sound producing device incorporated into eyeglasses 1520. In another embodiment, controller 22 issues the alert by sending a wireless message to another device, such as, but not limited to, a cell phone or a computer. The received message, in some embodiments, instructs the computer or cell phone to begin one or more of the assessment tests discussed above as part of step 102 (FIG. 5). The received message may alternatively or additionally instruct the computer or cell phone to take other steps, such as, for example, contacting one or more predetermined individuals or entities.

Multi-wavelength emitter 1658 emits light onto the wearers temple and photodetector 1660 detects a portion of the emitted light that is scattered by the tissue in the temple region of the wearer. Multi-wavelength emitters 1658 and photodetectors 1660 are operable to detect one or more of the following: (a) the wearer's heart rate, (b) a photoplethysmogram (PPG) (c) changes in surface tissue perfusion, and/or (d) cellular energy metabolism via cytochrome-a. The operation of emitters 1658 and photodetectors 1660 are described more completely in commonly assigned U.S. patent application Ser. No. 14/708,383, filed May 11, 2015, by inventors Marko Kostic et al. and entitled TISSUE MONITORING APPARATUS AND SYSTEM, the complete disclosure of which is incorporated herein by reference. Multiple sets of emitters 1658 and photodetectors 1660 may also be included in one or both of sensors arrays 1654 in order to detect a pulse wave velocity of the wearer, or other biological parameters of the wearer. Methods for detecting pulse wave velocity and other biological parameters of the wearer using such sets of emitters 1658 and photodetectors 1660 are disclosed in U.S. patent application Ser. No. 62/072,669, which was previously incorporated herein by reference in its entirety.

In some embodiments, controller 22 compares one or more parameters detected by the emitters 1658 and photodetectors 1660 of a first one of the sensors arrays 1654 to one or more of the same parameters detected by the emitters 1658 and photodetectors 1660 of the second sensor array 1654. Differences between these parameters that exceed a predetermined size threshold and/or that persist for longer than a predetermined time threshold may be indicative of a stroke. In such cases, controller 22 issues an alert in any of the manners previously described.

As noted, controller 22 may be installed on one of temple frame members 1652. In such cases, the outputs from the sensors on the sensor array 1654 opposite the temple frame member 1652 to which controller 22 is attached communicate with controller 22 using wireless communication. In one such embodiment, the communication is via Bluetooth. In other embodiments, different wireless protocols are used. In still other embodiments, a wire or other physical structure is used to couple the outputs of the first and second sensor arrays 1654 to a common controller 22.

In some embodiments of stroke detection device 1620, one or more of the sensors are coupled to a biasing structure that exerts a biasing force on the sensors to ensure contact with the wearer's skin. In other embodiments, the readings are taken regardless of any space that exists between the wearers skin and the sensors. Still further, in some embodiments, stroke detection device 1620 is modified to communicate with an auxiliary device, such as any one of the auxiliary devices described above, or to be an auxiliary device that communicates with a main device, such as any one of the main devices described above. For example, in some embodiments, stroke detection device 1620 communicates with a cell phone. In such cases, controller 22 forwards sensor data to be processed on a microcontroller inside the cell phone. Alternatively, controller 22 processes some or all of the sensor data locally and forwards the processed sensor data to the cell phone.

Figure 15:
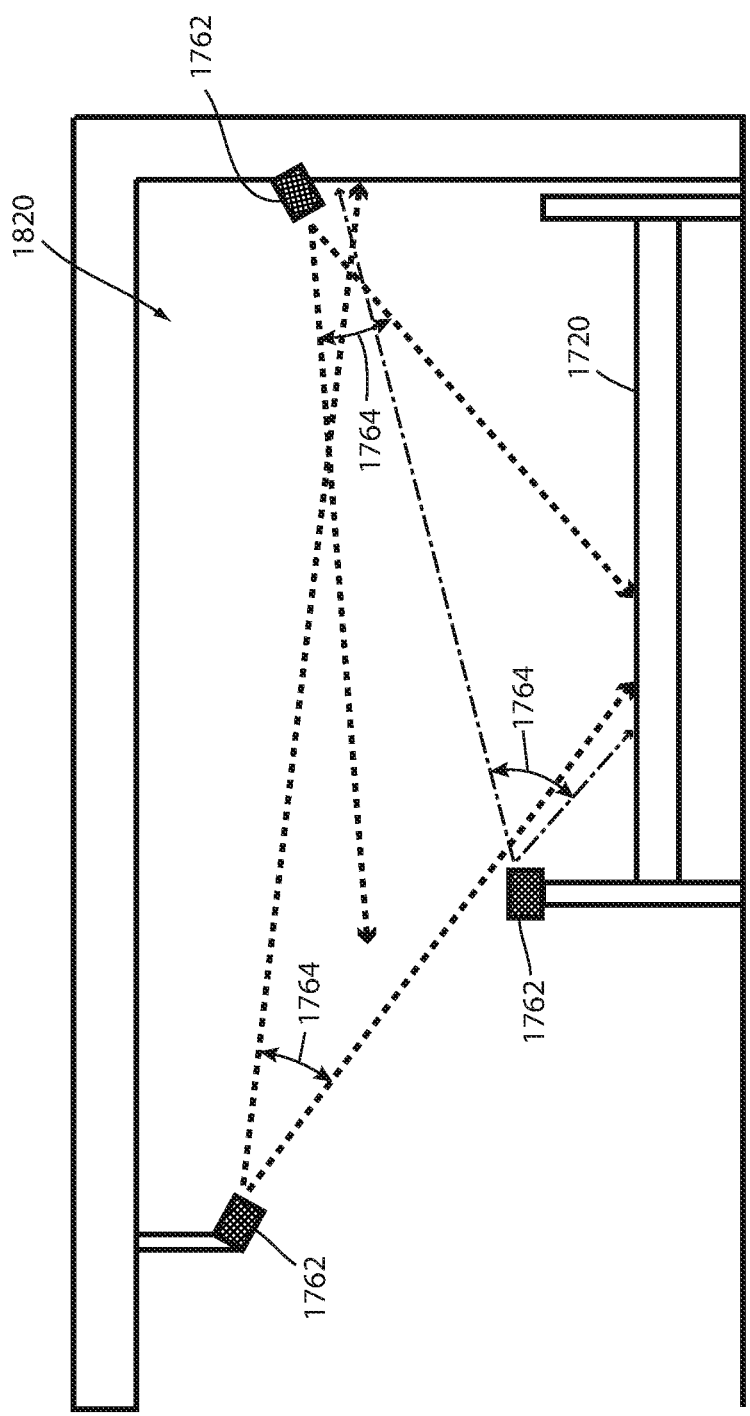
FIG. 15 is an elevation view of a tenth embodiment of a stroke detection device.
Figure 16:
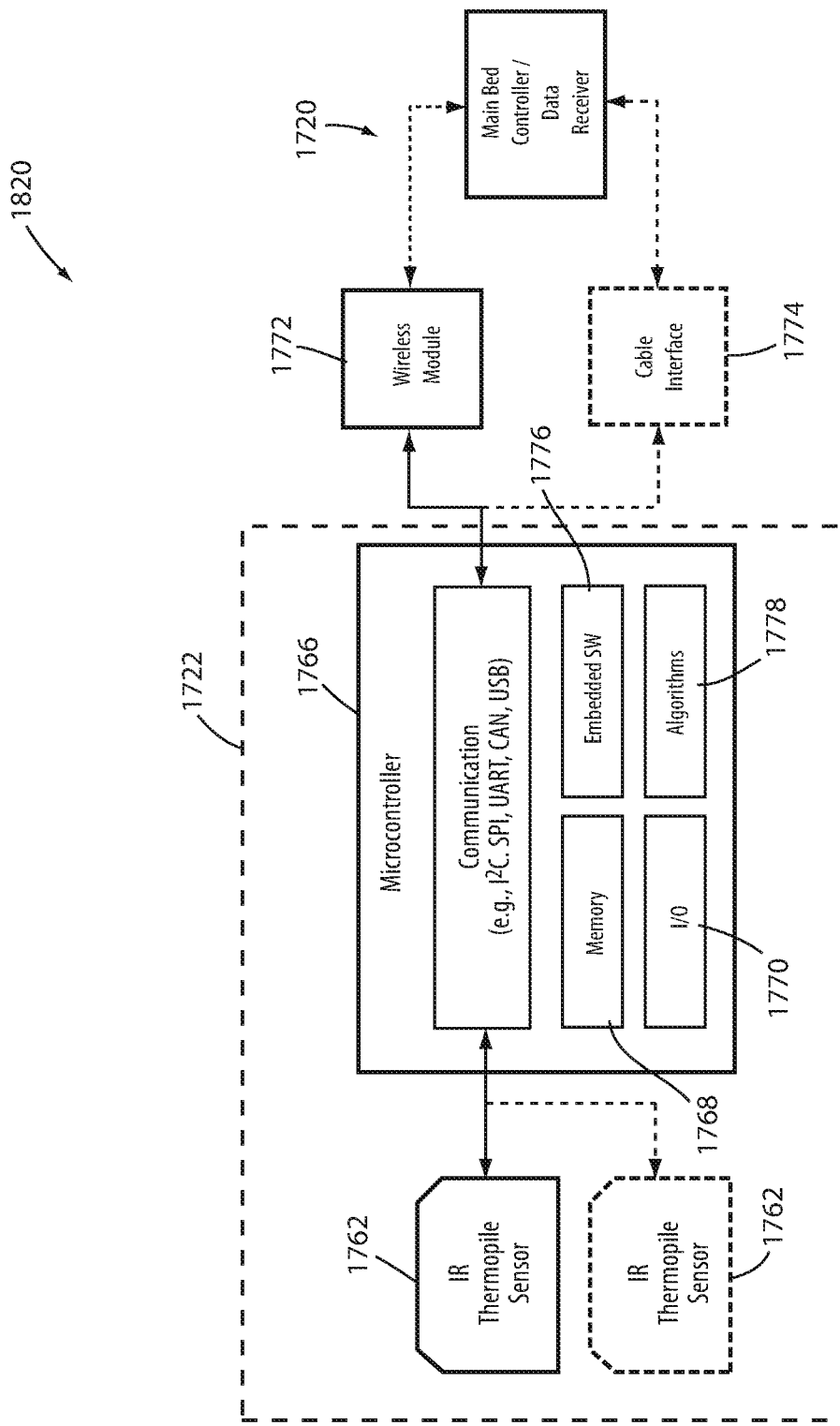
FIG. 16 is a block diagram of the stroke detection device of FIG. 14.

FIGS. 15 & 16 illustrate another alternative embodiment of a stroke detection device 1820 according to the present disclosure. Those components of stroke detection device 1820 that are common to one or more of the previously described stroke detection devices (20, 220, 420, 620, 820, 1020, 1220, 1420, and 1620) and that operate in the same manner as previously described are labeled in stroke detection device 1820 with the same reference number. Those components that are new are labeled with a new number, and those components that are similar, but modified in some way, bear the same reference number as found in the previously described stroke detection device but increased by two hundred. Stroke detection device 1820 includes a main device 1720 and one or more auxiliary devices 1722 (FIG. 16). Main device 1720 is physically implemented as a bed in FIG. 15, although it may be implemented in other physical forms in other embodiments, such as, but not limited to, a cot, a stretcher, a chair, an operating table, or some other type of person support apparatus.

Auxiliary device 1722 includes a plurality of thermopile sensors 1762 that are positioned at different locations with respect to main device 1720. Each thermopile sensor 1762 is adapted to detect thermal energy within a field of view 1764 of the thermopile sensor 1762. More specifically, the thermopile sensors 1762 are mid-range infrared sensors that measure surface temperatures of objects and people. They convert thermal energy into electrical signals to detect and track motion of a person positioned on the bed (main device 1720) of FIG. 15. Each thermopile sensor 1762 includes one or more thermopile detecting elements (pixels) that record temperature values within their own field of view 1764. In combination, the thermopile sensors 1762 collectively provide a map consisting of temperature values equal to the total number of pixels (which may vary depending upon the application and level of accuracy desired).

Auxiliary device 1722 includes an auxiliary controller 1766 that communicates with a memory 1768, one or more input/output ports 1770, and one or more wireless modules 1772 and/or cable interfaces 1774. Auxiliary controller 1766 also includes embedded software 1776 that, when executed by auxiliary controller 1766, carries out one or more algorithms 1778. Auxiliary controller 1766 uses the embedded software 1776 to execute one or more algorithms 1778 that determine the presence of a person on bed 1720, his or her position on bed 1720, and his or her movement.

Auxiliary controller 1766 uses motion detection algorithms to quantify the person's movement and compare the movement to normal values. If there is a change in the person's motion patterns during his or her sleep, auxiliary controller 1766 determines that an alert condition exists and takes any of the actions described above (e.g. makes an audible noise to awake the person and instructions to take one of the assessment tests described with respect to step 102). The test may be implemented using a user interface and display integrated into bed 1720, or it may be implemented on a cell phone that communicates with auxiliary device 1722. When implemented on the bed 1720, auxiliary device 1722 communicates with bed 1720 via either wireless module 1772 or via cable interface 1774. Regardless of where the test is implemented, the analysis and subsequent actions taken in response to the test may be carried out in the same manner as has been previously described.

In some embodiments, thermopile sensors 1762 are used that are constructed, and operate, in the same manner as described in commonly assigned U.S. patent application Ser. No. 14/692,871 filed on Apr. 22, 2015, by inventors Marko Kostic et al. and entitled PERSON SUPPORT APPARATUS WITH POSITION MONITORING, the complete disclosure of which is incorporated herein by reference. In other embodiments, other types of thermopile sensors 1762 are used.

One or more accelerometers may also be incorporated into bed 1720, either in conjunction with the use of thermopile sensors 1762 or separately from the use of thermopile sensors 1762. Such accelerometers are positioned to detect movement of the person support on bed 1720. Because strokes are often manifested by changed sleep movement patterns and, in some cases, changes in vital signs (heart rate, respiration, etc.), the outputs of the accelerometers are processed by a controller (e.g. main controller 22 or auxiliary controller 1766) in order to detect such changes in movement or vital signs. Appropriate alerting and/or testing is instituted as a result of such detection. The incorporation and use of accelerometers in beds to detect a person's vital signs is disclosed more fully in commonly assigned U.S. Pat. No. 7,699,784 issued to Wan Fong et al.

and entitled SYSTEM FOR DETECTING AND MONITORING VITAL SIGNS, the complete disclosure of which is incorporated herein by reference. The use of accelerometers for detecting a person's movement while positioned on a bed is disclosed in commonly assigned U.S. patent application Ser. No. 62/253,167 filed Nov. 20, 2015, by inventors Marko Kostic et al. and entitled PERSON SUPPORT APPARATUS WITH ACCELERATION DETECTION, the complete disclosure of which is incorporated herein by reference.

It will be understood that the principles disclosed herein can also be embodied as a software application in which instructions for one or more processors are tangibly and non-transitorily fixed in a computer-readable medium. The instructions, when executed by the one or more processors, carry out any one or more of the stroke detection functions described herein.

Various additional alterations and changes beyond those already mentioned herein can be made to the above-described embodiments. This disclosure is presented for illustrative purposes and should not be interpreted as an exhaustive description of all embodiments or to limit the scope of the claims to the specific elements illustrated or described in connection with these embodiments. For example, and without limitation, any individual element(s) of the described embodiments may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Any reference to claim elements in the singular, for example, using the articles "a," "an," "the" or "said," is not to be construed as limiting the element to the singular.

What is claimed is:

1. A stroke detection device comprising:
   a mobile phone comprising a main controller, a main memory, a micropohone, a main display, and a housing, the housing adapted to house the main controller, main memory, microphone and main display, the main controller adapted to execute a software application selected by a user of the mobile phone wherein the software application is stored in the main memory, and the microphone is adapted to detect a speech pattern of the user as measured while the user is talking into the mobile phone; and
   a removable case adapted to physically couple to the housing of the mobile phone and communicate with the mobile phone, the case comprising an auxiliary sensor integrated therein and adapted to detect a second characteristic of the user while the user is using the mobile phone, the second characteristic being one of the user's temperature or electrocardiogram, the case adapted to transmit data regarding the second characteristic to the mobile phone wherein the mobile phone is adapted to issue a notification to the user if either of the speech pattern or second characteristic indicates that the user may have experienced a stroke.

2. The stroke detection device of claim 1 wherein the case is in wireless communication with the mobile phone.

3. The stroke detection device of claim 1 wherein the case comprises no power source and is adapted to respond to a near field interrogation signal emitted from the mobile phone with a message, the message comprising the data regarding the second characteristic.

4. The stroke detection device of claim 1 wherein the auxiliary sensor comprises a plurality of temperature sensors and the second characteristic is a temperature difference between a right side of the user's body and a left side of the user's body.

5. The stroke detection device of claim 1 wherein the main controller issues instructions on the main display if either of the speech pattern or second characteristic indicates that the user may have experienced a stroke, the instructions corresponding to a test to be taken by the user using the stroke detection device.

6. The stroke detection device of claim 5 wherein the test comprises at least one of the following:
   (a) the user speaking a specific phrase into the microphone of the mobile phone wherein the main controller compares a current sound sample generated from the user speaking the specific phrase into the microphone to a past sound sample of the user speaking the specific phrase;
   (b) the user making a requested facial expression while a current image of the user is captured by an image sensor of the mobile phone, wherein the main controller compares the current image of the user to a past image of the user; and
   (c) the user attempting to hold his or her arm out straight while holding the mobile phone and the main controller monitors outputs from an accelerometer within the mobile phone while the user attempts to hold his or her arm out straight.

7. The stroke detection device of claim 6 wherein the main controller is further adapted take at least one of the following actions if the test indicates that the user may have experienced a stroke: (1) provide a warning on the main display encouraging the user to seek medical assistance, and (2) send a message to a health care worker indicating that the user may have experienced a stroke.

8. The stroke detection device of claim 1 wherein the mobile phone further comprises an image sensor, and wherein the software application is further adapted to cause the main controller to perform at least one of the following functions if the main controller determines that the user may have experienced a stroke while using the mobile phone:
   (a) instruct a user to speak a specific phrase into the microphone, after which the main controller compares a current sound sample generated from the user speaking the specific phrase into the microphone to a past sound sample of the user speaking the specific phrase, the past sound sample taken at a time prior to when the main controller determines that the user may have experienced a stroke; and
   (b) instruct the user to make a requested facial expression while a current image of the user is captured by the image sensor, after which the main controller compares the current image of the user to a past image of the user, the past image of the user taken at a time prior to when the main controller determines that the user may have experienced a stroke.

9. The stroke detection device of claim 8 wherein the software application causes the main controller, when executed, to perform both of the functions (a) and (b) after the main controller determines that the user may have experienced a stroke while using the mobile phone.

10. The stroke detection device of claim 9 wherein the main controller determines if the user may have experienced a stroke by detecting a change in the user's gait as detected by the main controller using outputs from a motion sensor incorporated into the stroke detection device.

11. The stroke detection device of claim 1 further comprising a second software application stored in the main memory and adapted to be executed by the main controller, wherein the second software application is adapted to enable the user to use the mobile phone to perform a function unrelated to detecting a stroke, and wherein the main controller is adapted to issue the notification while the user is using the mobile phone to perform the function.

* * * * *